United States Patent [19]
Fabijanski et al.

[11] Patent Number: 5,356,799
[45] Date of Patent: Oct. 18, 1994

[54] ANTISENSE GENE SYSTEMS OF POLLINATION CONTROL FOR HYBRID SEED PRODUCTION

[75] Inventors: Steven F. Fabijanski, Ottawa; Paul G. Arnison, Georgetown, both of Canada

[73] Assignee: Pioneer Hi-Bred International, Inc., Des Moines, Iowa

[21] Appl. No.: 892,635

[22] Filed: Jun. 2, 1992

Related U.S. Application Data

[63] Continuation of Ser. No. 306,438, Feb. 3, 1989, abandoned, which is a continuation of Ser. No. 151,906, Feb. 3, 1988, abandoned.

[51] Int. Cl.$^5$ ............ C12N 15/00; C12N 5/00; A01H 1/00; C07H 21/04
[52] U.S. Cl. ............ 435/172.3; 435/240.4; 536/24.1; 536/24.5; 47/58; 47/DIG. 1; 800/205; 800/250; 800/DIG. 15; 800/DIG. 17; 800/DIG. 40
[58] Field of Search ............ 435/172.3, 240.4; 800/205, 250, DIG. 15, DIG. 17, DIG. 40; 47/58, DIG. 1, 58.04; 536/27, 23.1, 23.2, 24.1, 24.5

[56] References Cited

U.S. PATENT DOCUMENTS

| | | | |
|---|---|---|---|
| 4,517,763 | 5/1985 | Beversdorf et al. | 47/58 |
| 5,107,065 | 4/1992 | Shewmaker et al. | 800/205 |

FOREIGN PATENT DOCUMENTS

| | | | |
|---|---|---|---|
| 0198288 | 10/1986 | European Pat. Off. | C12N 15/00 |
| 0223399 | 5/1987 | European Pat. Off. | C12N 15/00 |
| 0240208 | 10/1987 | European Pat. Off. | C12N 15/00 |
| WO88/05077 | 7/1988 | PCT Int'l Appl. | C12N 15/00 |

OTHER PUBLICATIONS

Sanders, P. 1987, Enzyme Microb. Technol. 9:250–1.
Kaluza et al., 1985. FEBS Lett. 188(1):57–42.
Mascarenhas et al. 1984. Theor. Appl. Genet. 68:323–326.
Horsch et al. 1984. Science 233:496–498.
Kamalay et al. 1984. Proc. Natl. Acad. Sci. USA 81:2801–2805.
Grill, L. 1983. Plant Molec. Biol. Rep. 1(1):17–20.
Ecker et al. 1986, Proc. Natl. Acad. Sci. USA 83:5372–5376.
Kim et al. 1985. Cell 42:129–138.
McCormick et al., Anther-Specific Genes: Molecular Characterization and Promoter Analysis in Transgenic Plants, 1989, Plant Reproduction: From Floral Induction to Pollination, Lord, E., Bernier, G., eds., ASPP Sympos., vol. 1, 128.
McCormick et al., Identification of Genes Specifically Expressed in Reproductive Organs of Tomato, 1987, Tomato Biotechnology, 255.
Stinson et al., Genes Expressed in the Male Gametophyte of Flowering Plants and Their Isolation, 1987, 83 Plant Physiol., 442.

(List continued on next page.)

Primary Examiner—David T. Fox
Attorney, Agent, or Firm—Foley & Lardner

[57] ABSTRACT

A process is described for producing hybrid seed using male-sterile plants created by employing molecular techniques to manipulate antisense DNA and other genes that are capable of controlling the production of fertile pollen in plants. Transformation techniques are used to introduce constructs containing antisense DNA and other genes into plants. Said plants are functionally male-sterile and are useful for the production of hybrid seed by the crossing of said male-sterile plants with pollen from male-fertile plants. Hybrid seed production is simplified and improved by this invention and can be extended to plant crop species for which commercially acceptable hybrid seed production methods are not currently available.

32 Claims, 8 Drawing Sheets

OTHER PUBLICATIONS

Mascarenhas, Characterization of Genes that are Expresses in Pollen, 1989, The Molecular Basis of Plant Development, 99.

Gasser et al., Analysis of Floral Specific Genes, 1988, Journal of Cellular Biochemistry Supplement 12C, Abstract L021.

Gasser et al., Isolation of Tissue-Specific cDNAs from Tomato Pistils, 1989, The Plant Cell, vol. 1, 15.

Izant & Weintraub, Constitutive and Conditional Suppression of Exogenous and Endogenous Genes by Anti-Sense RNA, 1985, Science, V.229, 345.

Weintraub et al., Anti-sense RNA as a Molecular Tool for Genetic Analysis, 1986, Trends in Genetics, vol. 1, 1.

McGarry & Lindquist, Inhibition of Heat Shock Protein Synthesis by Heat-Inducible Antisense RNA, 1986, 83 PNAS, 399.

Rothstein et al., Stable and Heritable Inhibition of the Expression of Nopaline Synthase in Tobacco Expressing Antisense RNA, 1987 84PNAS, 8439.

Sandler et al., Inhibition of Gene Expression in Transformed Plants by Antisense RNA, 1988 Plant Molecular Biology 11:301-310.

Delauney et al., A Stable Bifunctional Antisense Transcript Inhibiting Gene Expression in Transgenic Plants, 1988 85 PNAS, 4300.

Simpson et al., Light-Inducible and Tissue-Specific Expression of a Chimaeric Gene Under Control of the 5'-Flanking Sequence of a Pea Chlorophyll a/b-binding Protein Gene, 1985, 4 EMBO, Journal No. 11, 2723.

Nagy et al., Photoregulated Expression of Pea rbcS Gene in Leaves of Transgenic Plants, 1985, 4 EMBO Journal No. 12, 3063.

Medford & Klee, Manipulation of Auxin, Cytokinin and Gus Levels Using the Maize HSP70 Promoter, 1988, Journal of Cellular Biochemistry Supplement 12C, Abstract L616.

Callis et al., *Genes & Development* 1:1183-1200 (1987).

Chee et al., *Gene* 41:47-57 (1986).

Moffat et al., *Plant Physiology* 86:1150-1154 (1988).

Sawhney et al., *Can. J. Bot.* 66:2013-2021 (1988).

FIG. 2a

```
              10         20         30         40         50         60         70         80
Dde I   _TTCATTTTTCCTTTAAGTAAATAAAAAGGTATGTGTCCTATGCGTGTACATAAATCTGATGTTTTCAAAAAGTTATTGCTA
(-1200)- AAGTAAAAGGAAATTCATTTATTTTTCCATACACAGGATACGCACATGTATTTAGACTACAAAAGTTTTTCAATAACGAT 90        100        110        120        130        140        150        160
         TTTTTAGAATTATGAATTTATTTAAAACAATGTCAATAAAAATATTTTTCAAATATTACTATTTAAATTAATAGGTTATTA
         AAAAATCTTAATACTTAAATAAATTTTGTTACAGTTATTTTATAAAAAGTTTATAATGATAAATTTAATTATCCAATAAT 170        180        190        200        210        220        230        240
         GGTGGATGTCCACACGTAACATAATTTATAAGATTATATGAAAAAAATAGTAAGTATTTAATTAAATTTTTTACTCATT
         CCACCTACAGGGTGTGCATTGTATTAAATATTCTAATATACTTTTTTTATCATTCATAAATTAATTTAAAAAAATGAGTAA
                                                                 EcoRI
             250        260        270        280        290 ↓    300        310        320
         CAATAAAAATAACAAAAAATGAAAACTATATAATAATCAGATAGATGAATTGAATTCTAAAAATAGCAATAACTTTTTGAG
         GTTATTTTATTGTTTTTTACTTTTGATATATTATTAGTCTATCTACTTAACTTAAGATTTTTATCGTTATTGAAAAACTC 330        340        350        360        370        380        390        400
         AACATCAGATTTATGTACACGCATAGGACACATACCTTTTTATTTACTTAAAGGAAAATGAACGAGTCTAAATCTTCCAC
         TTGTAGTCTAAATACATGTGCGTATCCTGTGTATGGAAAAATAAATGAATTTCCTTTTACTTGCTCAGATTTAGAAGGTG 410        420        430        440        450        460        470        480
         ATGTTATATGAGCAAAACATGAATTTTTCTAAATTAGATTCGTTTAAATCAGAACATATTAATGTGAGTTTCTTAAATTA
         TACAATATACTCGTTTTGTACTTAAAAAGATTTAATCTAAGCAAATTTAGTCTTGTATAATTACACTCAAAGAATTTAAT
                                                                → Start of Transcription
             490        500        510        520       ↓ 530       540        550        560
         GATTTTTAATATCTATATATACGTAAGAATACTTCTTATGTTTTAAAATAAAAAATAGAATACTTCATCTCTTTCCTAAA
         CTAAAAATTATAGATATATATGCATTCTTATGAAGAATACAAAATTTTATTTTTTATCTTATGAAGTAGAGAAAGGATTT
                                                  Dde I
             570        580        590       ↓ 600        610        620        630        640
         TTTTTAAGCCAATATCAATCCATTTCTATAATCTAACATCAAGAAATCCCTTCAACTCTCTTTTTCGTTCTTAATTATCT
         AAAAATTCGGTTATAGTTAGGTAAAGATATTAGATTCTACTTCTTTAGGGAAGTTGAGAGAAAAAGCAAGAATTAATAGA
         Exon 1   Intron 1
             650     ↔               70         680        690        700        710        720
         CCATCATTCTCTCACATGGTTTGTATTTTCATCTTAATATATTGCATATAGTAATTCCATAATAAATTGATTATACTAAA
         GGTAGTAAGAGAGTGTACCAAACATAAAAGTAGAATTATATAACGTATATCATTAAGGTATTATTTAACTAATATGATTT
                         Hinc II
             730        740 ↓      750        760        770        780        790        800
         ATTTGACTTTTAAAATATTGTCAACCCCCATATAATAAATTTTATTTACTATATAAAACATAGCATTAAATTATCTCTTT
         TAAACTGAAAATTTTATAACAGTTGGCGGTATATTATTTAAAATAAATGATATATTTTGTATCGTAATTTAATAGAGAAA 810        820        830        840        850        860        870        880
         GTGTAAAATTCATAACTTTGCAGAAGGCTAGAAAATATAGATAGTATAGTCAGAAATGTTTGCGTTAAAATTGAAAGGAT
         CACATTTTAAGTATTGAAACGTCTTCCGATCTTTTATATCTATCATATCAGTCTTTACAAACGCAATTTTAACTTTCCTA 890        900        910        920        930        940        950        960
         CAACCATGGAGTATTTAAATGTTTTTTATACTTTTATGCCATTTATAATTTTTTTAATGTATGGGTTTATATATGATGAAG
         GTTGGTACCTCATAAATTTACAAAAAATATGAAATACGGTAAATATTAAAAAAATTACATACCCAAATATATACTACTTC 970        980        990       1000       1010       1020       1030       1040
         AACTATTATGATAAAATAATATTAAATAATTTCATTTTTATCATCTATTTATGAACATTTGTCCTGCACATACAAATGA
         TTGATAATACTATTTTATTATAATTTATTAAAGTAAAAATAGTAGATAAATACTTGTAAAACAGGACGTGTATGTTTACT 1050       1060       1070       1080       1090       1100       1110       1120
         TTTAACCAACATTTTTAATAATATGGATGAACTATAGCTCTTACGTAAATTTATTTGATATTTTTAATTAAATTTATATA
         AAAATTGGTTGTAAAAATTATTATACCTACTTGATATCGAGAATGCATTTAAATAAACTATAAAAATTAATTTAAATATAT
```

FIG. 2b

```
       1130      1140      1150      1160      1170      1180      1190      1200
TTTTTATAGGTAATTTGTTATGCTTTTTCCAATACATACAGTAGTTGTTATTAAAATATCAAAATTTAATACGTAATGTTT
AAAAATATCCATTAAACAATACGAAAAGGTTATGTATGTCATCAACAATAATTTTATAGTTTTAAATTATGCATTACAAA 1210      1220      1230      1240      1250      1260      1270      1280
ATTAATATGCACACAATTCTTAAAACCATATTTTTAAAAAATAATGTGTGACCAAACGATATGCTCATTTTTTTATTTAC
TAATTATACGTGTGTTAAGAATTTTGGTATAAAAATTTTTTATTACACACTGGTTTGCTATACGAGTAAAAAAATAAATG 1290      1300      1310      1320      1330      1340      1350      1360
TAGCAAAATATATTTCTTTTCTTACTTATAACGTTTAAAAAGAAATGTTATTAAACATTTTTTGCTGATAAATAAATTTT
ATCGTTTTATATAAAGAAAAGAATGAATATTGCAAATTTTTCTTTACAATAATTTGTAAAAAACGACTATTTATTTAAAA
                                                                        Exon 2
       1370      1380      1390      1400      1410      1420     ⌐  1430      1440
ATATTTCATAAAATCTAAATATATTTTTTAACAATTAAAATTTGAAATTTTTATATCTTACAGGAATGATGGCAGATGCG
TATAAAGTATTTTAGATTTATATAAAAAATTGTTAATTTTAAACTTTAAAAATATAGAATGTCCTTACTACCGTCTACGC 1450      1460      1470      1480      1490      1500      1510      1520
CAGAAAAAGAATTGTCCTCATAAAATTCCAATAAAAGGAAGTTATTGTGCTCCAACTATATGTTTGGATATGTGTAAGAA
GTCTTTTTCTTAACAGGAGTATTTTAAGGTTATTTTCCTTCAATAACACGAGGTTGATATACAAACCTATACACATTCTT
                   Intron 2
       1530      1540 ⌐  1550      1560      1570      1580      1590      1600
GCAACATGGAACTGTTGGTAGTTGTGCGGAATAAAAATGATTTGTAACTGCGCTTGTAAGTAAGCGTTCTCACTAAGTG
CGTTGTACCTTGACAACCATCAACACGCCTTATTTTACTAAAACATTGACGCGAACATTCATTCCCAAGAGTGATTCAC 1610      1620      1630      1640      1650      1660      1670      1680
TTATGAATCTAGTAATGTCCAACCAAAGTTTTATATTATTTCTTTTAACAATAAGTCTAAATGTTTGTCTCAGATTTGTG
AATACTTAGATCATTACAGGTTGGTTTCAAAATATAATAAAGAAAATTGTTATTCAGATTTACAAACAGAGTCTAAACAC 1690      1700      1710      1720      1730      1740      1750      1760
GATCTATTTATAATAAATAATAATATGAATGTTAAATAAATACAAATGTGTAAAACAAGAGTGGACTATTAATAAAAATAT
CTAGATAAATATTATTTATTATTATACTTACAATTTATTTATGTTTACACATTTGTTCTCACCTGATAATTATTTTATA 1770      1780      1790      1800      1810      1820      1830      1840
ATGATTACATTATTGTTAGAAGTAACCAATATTACGTGTAAAATCAAAATCTTAAGACAAGTTAAAAAGATTGAGATGAA
TACTAATGTAATAACAATCTTCATTGGTTATAATGCACATTTTAGTTTTAGAATTCTGTTCAATTTTTCTAACTCTACTT 1850      1860      1870      1880      1890      1900      1910      1920
ATCACAACCAATATTTAAATGTGAGATAATCAACTAACATGTAATTTTGTACACATTGTAAAAAAAAAAAAGCAAGAGTT
TAGTGTTGGTTATAAATTTACACTCTATTAGTTGATTGTACATTAAAACATGTGTAACATTTTTTTTTTTTCGTTCTCAA 1930      1940      1950      1960      1970      1980      1990      2000
CATTATCAAACAAGAAAGTGTTAGAAAGAGCAACAGATTCATTGCAAGGGCAGTCTAGGTTGAATTGCCTTGACATAGCG
GTAATAGTTTGTTCTTTCACAATCTTTCTCGTTGTCTAAGTAACGTTCCCGTCAGATCCAACTTAACCGAACTGTATCCC 2010      2020      2030      2040      2050      2060      2070      2080
AAAATTGAAAGCACTGTTTCTGAACATGACAACGCTTGGTCAGGAAGAACAATCTCACAACCAGAGTTTGGGTAGATTT
TTTTAACTTTCGTGACAAAGACTTGTACTGTTGCGAACCAGTCCTTCTTGTTAGAGTGTTGGTCTCAAAACCCATCTAAA
                                                                    ----Exon 3
       2090      2100      2110      2120      2130      2140          2150      2160
CTCCAATGTCATTATCAGGTACGAGTTATGACTTCATCCACATCTCAGTCCCAGTTCCCTTCTCAGGAAGTTCCTTG
GAGGTTACAGTAATAGTCCATGCTCAATACTCTGAAGTAGGTGTAGAGTCAGGGTCAACGGAAGAGTCCTTCAAAGGAAC 2170      2180      2190      2200      2210      2220      2230      2240
ACGAAGGAGGTTATTACAGAAAGCTAAGTTACATGAGCCTGACATATCATGCAAGGGCAGTCCCAACAAGAAAATGTTAG
TGCTTCCTCCAATAATGTCTTTCGATTCAATGTACTCGGACTGTATAGTACGTTCCCGTCAGGGTTGTTCTTTTACAATC
```

FIG. 2c

```
     2250       2260       2270       2280       2290       2300       2310       2320
AAAGAGCAACATATCATGCAAGGACAGTCCAGGTTTGAATTGCCTTGACAGATGGTTTGCAGACATGCCATCTGAAGGTC
TTTCTCGTTGTATAGTACGTTCCTGTCAGGTCCAAACTTAACGGAACTGTCTACCAAACGTCTGTACGGTAGACTTCCAG 2330       2340       2350       2360       2370       2380       2390       2400
CTACAAACTCATCAGACAACGAAGGAAAATTGATAGCATTGTTTCTGAACATGACAAAACTCTAGTCAGGAAGAAGAATC
GATGTTTGAGTAGTCTGTTGCTTCCTTTTAACTATCGTAACAAAGACTTGTACTGTTTTGAGATCAGTCCTTCTTCTTAG

Sst I
     2410       2420       2430       2440       2450       2460       2470       2480
TCACAACCAAAGTTTTGGGTAGAGCTC
AGTGTTGGTTTCAAAACCCATCTCGAG
```

FIG. 2d

```
          10         20         30         40         50         60         70         80
CCAACAGCAAAACTACTTCAGTTATATCCGTATTTGCCTTTTAAACGATAATAANAAAATATAGCAAAAAATATTAAATTT
GGTTGTCGTTTTGATGAAGTCAATATAGGCATAAACGAAAATTTGCTATTATINTTTTATATCGTTTTTTATAATTTAAA 90        100        110        120        130        140        150        160
GAAACATTGCCGTTTCACCTGAAATTAACCCGCAAACCCCTNGTTACCATATGTTAATTACCTAGAACATTGAAAAACAA
CTTTGTAACGGCAAAGTGGACTTTAATTGCCCGTTTGCGGANCAATGGTATACAATTAATGGATCTTGTAACTTTTTGTT 170        180        190        200        210        220        230        240
ATTTAATATCTACCACCAAATATAGATGAACTATAAATTATCTACAACATCCATCTCTCTATATCGGAAGCTCTCTCGTT
TAAATTATAGATGGTGGTTTATATCTACTTGATATTTAATAGATGTTGTACGTAGAGAGATATAGCCTTCGAGAGAGCAA 250        260        270        280        290        300        310        320
CATCCGGATCCGTTCCTTTCCGGTCATTTTCTCTCTCCGGTCCATAGGAGAACATCCGATCATGATCACTCCGATCAAACT
GTACGGCCTAGCCAACGAAAGCCCAGTAAAAGAGAGAGGCCAGGTATCCTCTTGTAGGCTAGTACTAGTGAGGCTAGTTTGA 330        340        350        360        370        380        390        400
AGCCTTTCTCTTATTATTCATCACCACAACAGCAACCGCTTGCACCCAAAGCCAAACGCAGGAACTACCTTTTCACACCGC
TCGGAAAGAGAATAATAAGTAGTCGGTGTTGTCGTTGCCGACGTCCGTTTCCGTTTCCGTCCTTGATCGAAAAGTGTCCCG 410        420        430        440        450        460        470        480
ATGCAAAAGCAGTCCGGAATATGCCACTGTTGTCCTAACAAACACAAGTCCATGCCTGTAAAACCCTTAAACACGTTCCTA
TACGTTTTCGTCACCGCCTTATACGTGACAACAGGATTGTTTGTGTTCAGGTACGACATTTTCGGAATTTGTGCAAGGAT 490        500        510        520        530        540        550        560
CCGATGACCCTATCGAATTGATCGGAGCGTTAGCGGCTGCGACTGAATCTTCTGTGAAAAGAAGTGTGGTTTTCCTCTCC
GGCTACTCGGGATAGCTTAACTAGCCTCGCAATCGCCGACGCCTGACTTAGAAGACACTTTTCTTCACACCAAAGGAGACG 570        580        590        600        610        620        630        640
GAGATCAAACCAAAACACAAATCAAACGCAACCGCAGCTGCAGTCGTCAACAGCTGCGAAAAAAACTTGAAGTACGCATT
CTCTAGTTTGGTTTTGTGTTTAGTTTGCGTTGGCGTCGACGTCACCAGTTGTCGACCCTTTTTTTGAACTTCATCGGTAA 650        660        670        680        690        700        710        720
AGAAGATTTCACTGATTTTTGGAACGCTATGCGGAAAGATGTAAAGACGTTGCCTCATAACTATTTCACGTGTAAGAAGA
TCTTCTAAAGTGACTAAAAACCTTGCGATACCCTTTCTACATTTCTGCAACCGAGTATTGATAAAGTGCACATTCTTCT 730        740        750        760        770        780        790        800
AGTTAATGTCGATCATCGGGTACCATTCGGACTTGTTTCGATGATATTCGATGATAAGAATCTGTTGAAGGAANTGGAGACT
TCAATTACAGCTAGTACCCCATGGTAACCTGAACAAACCTACTATAACTACTATTCTTAGACAACTTCCTTNACCTCTGA 810        820        830        840        850        860        870        880
CCGATTAGTGTTCCGAAGAATCTAAGCAGTAATACGTATGATGTGTTTAATGGTTTGAAAACTATTTTTAAGACGTTTCG
CCCTAATCACAACCCTTCTTAGATTCGTCATTATCCATACTACACAAATTACCAAACTTTTGATAAAAATTCTGCAAACC 890        900        910        920        930        940        950        960
TATCAAGGTGAAACTTAACGAGGAAGACACTTGCCCCCAACCGCCACCATTGTCGAATTATTACTACTGATTAAATGATT
ATAGTTCCACTTTGAATTGCCTCCTTCTCGTGAAGCGGGCGTTGCCGGGTGGTAACAGCCTTAATAATGATGACTAATTTACTAA 970        980        990       1000       1010       1020       1030       1040
TGGATGTAATAAATAATTAATATCACTCGTATAATGCCTAAAGCGACCATATATGTACGATGTATGTTCTAGGTTTTATA
ACCTACATTATTTATTAATTATAGTGAGCATATTACGGATTTCGCTGGTATATACATGCTACATACAAGATCCAAAATAT 1050       1060       1070       1080       1090       1100       1110       1120
CATGTACCGATGGATTTCGAGATGATTGCAAAGGATATATTAATGGAATGTGAGTTTTTTTATAAGTTTTTGAATTGTCA
GTACATGCCTACCTAAAGCTCTACTAACCTTTTCCTATATAATTACCTTACACTCAAAAAAAATATTCAAAAACTTAACAGT
```

FIG. 2e

```
        1130      1140      1150      1160      1170      1180      1190      1200
TCAAAATGAAGCTGAAAGTATATATGTTGATTACATAATTATTTGATAGACCTTGATAACTCGAACAAATATACTATCGC
AGTTTTACTTCGACTTTCATATATACAACTAATGTATTAATAAACTATCTCGGAACTATTGAGCTTGTTTATATGATAGCG 1210      1220      1230      1240      1250      1260      1270      1280
AATCATTATTGGTTAAATGTTTTCGGATACATGTCCTACGTCAAACAAAATAATTGTGCATTTTTCATATATTTGATGCA
TTAGTAATAACCAATTTACAAAAGCCTATGTACAGGATGCAGTTTGTTTTATTAACACGTAAAAAGTATATAAACTACGT 1290      1300      1310      1320      1330      1340      1350      1360
TGAAAGTTTCATATATTTGATGATGAAACCATGCATTTGTTTCTTGTGCCTCCCGGGACTTGTCAACATTCAACGAACCT
ACTTTCAAAGTATATAAACTACTACTTTGGTACGTAAACAAAGGAACACGAGGGCCCTGAACAGTTGTAAGTTCCTTCGGA 1370      1380      1390      1400      1410      1420      1430      1440
TCAGTAATCAACTACATATGATACTGATCTAGATGATGTATGTACATGTACGACCATGCATGAATCACGCCGATGTTTCT
AGTCATTAGTTGATGTATACTATGACTAGATCTACTACATACATGTACATGCTCGGTACGTACTTAGTGCGGCTACAAAGA 1450      1460      1470      1480      1490      1500      1510      1520
TTTATCAAGGCGATGTTTAAAATGTACCCCGCTTTCTCGTTCTGGTAGGTATAAATACGAGTGAAATAACATTCCTATGT
AAATAGTTCCGCTACAAATTTTACATGGGGCGAAAGAGCAAGACCATCCATATTTATGCTCACTTTATTGTAAGGATACA 1530      1540      1550      1560      1570      1580      1590      1600
ATAGTATAGTAGTTCATTTTGTTGACCAAAATTTAAATATATAGGACATAATTATATTTTCTCAAATGAATTTGAGTTTT
TATCATATCATCAAGTAAAACAACTGGTTTTAAATTTATATATCCTGTATTAATATAAAAGAGTTTACTTAAACTCAAAA 1610      1620      1630      1640      1650      1660      1670      1680
GAGTGCCTCCTGAAAAGATGATTCCAGCTTTTCAATTTTACAATGCTGCGGTCAACCCCCCCAAGTATTATCGTTTATAAAAA
CTCACGGAGGACTTTTCTACTAAGGTCGAAAGTTAAAATGTTACGACCCAGTTGCCGCCGGTTCATAATAGCAATATTTTT 1690      1700      1710      1720      1730      1740      1750      1760
AATACTCAGAATAATCTCACACCTAAAACTGCGCATGAACTTGTTAATAGTCTAAAAAGATGTCCATGAACTGAATGAAT
TTATGAGTCTTATTAGAGTGTGGATTTTGACGCGTACTTGAACAATTATCAGATTTTTCTACAGGTACTTGACTTACTTA 1770      1780      1790      1800      1810      1820      1830      1840
AATACCATTCATGTTTGAGTAACACCATAGATGACACAATTTTCTTACTACCACTAATAGATGACACAATTGTCTTTGTT
TTATGGTAAGTACAAACTCATTGTGGTATCTACTGTGTTAAAAGAATGATGGTGATTATCTACTGTGTTAACAGAAACAA
                                                          Hind III
        1850      1860      1870      1880      1890       ↓        1910      1920
ACATGTTGTAGTGTCCGATTAATTTGGGTTGAAGAAGATGAGAACTCTCGATGAGAAGCTTTAGAAAAATGCATTTACTT
TGTACAACATCACAGGCTAATTAAACCCAACTTCTTCTACTCTTGAGAGCTACTCTTCGAAATCTTTTTACGTAAATGAA 1930      1940      1950      1960      1970      1980      1990      2000
TCGTTACTTTCGAAATTGGGATGTAAAACTAGTACTACGGAATGAAAATCCCAAAATAAGTTGTTTATTCTCTCTAATCCT
AGCAATGAAAGCTTTAACCCTACATTTTGATCATGATCCTTACTTTTAGCGTTTTATTCAACAAATAAGAGAGATTAGGA 2010      2020      2030      2040      2050      2060      2070      2080
AAAATTAATAAAATTATAATAGACTAACTTTTCCATCCTTAAGTTACTTCTTATTTTTAGTAATCGAAGCTACACCTCTT
TTTTAATTATTTTAATATTATCTGATTGAAAAGGTAGGAATTCAATGAAGAATAAAAATCATTAGCTTCGATGTGGAGAA 2090      2100      2110      2120      2130      2140      2150      2160
GATCAGGACAAAGACATAATCAAATCATCTTGTGGTGAATAATTTTTAATCTCAAATCCAATATTTGATTAGAGAAGTTT
CTAGTCCTGTTTCTGTATTAGTTTAGTAGAACACCACTTATTAAAAATTAGAGTTTAGGTTATAAACTAATCTCTTCAAA 2170      2180      2190      2200      2210      2220      2230      2240
CAGCCATTCAACTACCTAAAATGTCTCCCTCCATCCAAAGCTCATGCGAAATAATTTT  —  Hind III
GTCGGTAAGTTGATGGATTTTACAGAGGAGGTACGTTTCGAGTACGCTTTATTAAAA  —  (bp 3200)
```

ANTISENSE GENE SYSTEMS OF POLLINATION CONTROL FOR HYBRID SEED PRODUCTION

This application is a continuation of application Ser. No. 07/306,438, filed Feb. 3, 1989, now abandoned; which is a continuation of application Ser. No. 07/151,906, filed Feb. 3, 1988 now abandoned.

BACKGROUND OF THE INVENTION

The present invention relates to a method for producing male sterile plants and hybrid seed, to genetic material used to impart the male sterility trait and to new products produced by said method, namely, genetically transformed plants carrying the male sterile trait, male sterile plants and hybrid seed produced by pollinating said plants with pollen from male fertile plants.

Production of hybrid seed for commercial sale is a large industry. Hybrid plants grown from hybrid seed benefit from the heterotic effects of crossing two genetically distinct breeding lines. The agronomic performance of this offspring is superior to both parents, typically in rigour, yield, and uniformity. The better performance of hybrid seed varieties compared to open-pollinated varieties makes the hybrid seed more attractive for farmers to plant and thereby commands a premium price in the market place.

In order to produce hybrid seed uncontaminated with selfed seed pollination control methods must be implemented to ensure cross-pollination and not self-pollination. Pollination control mechanisms can be mechanical, chemical, or genetic.

A simple mechanical method for hybrid seed production can be used if the plant species in question has spatially separate male and female flowers or separate male and female plants. The corn plant, for example, has pollen producing male flowers in an inflorescence at the apex of the plant and female flowers in the axils of leaves along the stem. Outcrossing is assured by mechanically deasselling female plants to prevent selfing.

Most major crop plants of interest, however, have both functional male and female organs within the same flower so emasculation is not a simple procedure. It is possible to remove by hand the pollen forming organs before pollen shed, however this form of hybrid seed production is extremely labour intensive and hence expensive. Seed is produced in this manner if the value and amount of seed recovered warrants the effort.

A second general method of producing hybrid seed is to use chemicals that kill or block viable pollen formation. These chemicals, termed gametocides, are used to impart a transitory male-sterility. Commercial production of hybrid seed by use of gametocides is limited by the expense and availability of the chemicals and the reliability and length of action of the applications. These chemicals are not effective for crops with an extended flowering period because new flowers will be produced that will not be affected. Repeated application of chemicals is impractical because of costs.

Many current commercial hybrid seed production systems for field crops rely on a genetic method of pollination control. Plants that are used as females either fail to make pollen, fail to shed pollen or produce pollen that is biochemically unable to effect self-fertilization. Plants that are unable (by several different means) to self pollinate biochemically are termed self-incompatible. Difficulties associated with the use of self-incompatibilities are: availability and propagation of the self-incompatible female line and stability of the self-incompatibility. In some instances self-incompatibility can be overcome chemically or immature buds can be pollinated by hand before the biochemical mechanism that blocks pollen is activated. Self-incompatible systems that can be deactivated are often very vulnerable to stressful climatic conditions that break or reduce the effectiveness of the biochemical block to self-pollination.

Of more widespread interest for commercial seed production are systems of pollen control based on genetic mechanisms causing male sterility. These systems are of two general types: (a) genic male sterility, which is the failure of pollen formation because of one or more nuclear genes or (b) cytoplasmic-genetic male sterility (commonly called cytoplasmic male sterility or CMS) in which pollen formation is blocked or aborted because of a defect in a cytoplasmic organelle (mitochondrion).

Nuclear (genic) sterility can be either dominant or recessive. A dominant sterility can only be used for hybrid seed formation if propagation of the female line is possible (for example, via in vitro clonal propogation). A recessive sterility could be used if sterile and fertile plants are easily discriminated. Commercial utility of genic sterility systems is limited however by the expense of clonal propogation and roguing the female rows of self-fertile plants.

Many successful hybridization schemes involve the use of CMS. In these systems, a specific mutation in the cytoplasmically located mitochondrion can, when in the proper nuclear background, lead to the failure of mature pollen formation. In some other instances, the nuclear background can compensate for the cytoplasmic mutation and normal pollen formation occurs. The nuclear trait that allows pollen formation in plants with CMS mitochondria is called restoration and is the property of specific "restorer genes". Generally the use of CMS for commercial seed production involves the use of three breeding lines, the male-sterile line (female parent), a maintainer line which is isogenic to the male-sterile line but contains fully functional mitochondria and the male parent line.

The male parent line may carry the specific restorer genes (usually designated a restorer line) which then imparts fertility to the hybrid seed. For crops (e.g. vegetables) for which seed recovery from the hybrid is unimportant, a CMS system could be used without restoration. For crops for which the fruit or seed of the hybrid is the commercial product then the fertility of the hybrid seed must be restored by specific restorer genes in the male parent or the male-sterile hybrid must be pollinated. Pollination of non-restored hybrids can be achieved by including with hybrids a small percentage of male fertile plants to effect pollination. In most species, the CMS trait is inherited maternally (because all cytoplasmic organelles are inherited from the egg cell only), which can restrict the use of the system.

In a crop of particular interest herein, the oilseed crop of the species *Brassica napus* or *Brassica campestris*, commonly referred to as Canola, no commercial hybrid system has been perfected to date. Mechanical emasculation of flowers is not practical for hybrid seed production on any scale. The use of currently available gametocides is impractical because of the indeterminate nature of flower production. Repeated application of chemicals is expensive and the method is prone to contamination with selfed seed.

Genes that result in self-incompatibility are quite widespread in Brassica species and self-incompatible hybrid systems have been used for hybrid seed production in vegetables. Major difficulties are associated with the propagation of the female lines and the breakdown of self-incompatibilities under stressful conditions. Adaptation of these systems to Brassica oilseeds is restricted by the expense of increasing the female lines and the availability of appropriate self-incompatible genes in the dominant Canola species, *Brassica napus*.

A variety of sources of male sterility are available in Brassica species. Both recessive and dominant genic systems have been reported, however their use is restricted because large scale in vitro propagation or roguing of female lines is in most cases impractical for large scale seed production.

Additionally, a number of CMS systems have been reported in Brassica species. Four of these systems have been explored as possible vehicles for hybrid seed production: pol, nap, anand and ogu. The Polima system (pol) has been widely studied and is probably the closest to commercial use. Good restoration and maintenance of pol CMS has been achieved, however the system suffers from potential instability of the CMS with high temperature, a reduction in the heterotic effect of crossing different lines (because of the defective mitochondria) and a reduction in hybrid seed oil content. The use of other CMS systems is also restricted by heat sensitivity (nap), difficulty in restoration of fertility (ogu, anand), difficulty in the maintenance of the sterility (nap) and low temperature chlorosis associated with the sterile cytoplasm (ogu). Improvement of these systems is the object of considerable research, however all of the systems have some inherent weaknesses that limit their utility.

An ideal system for hybrid seed production in any crop would be a form of genic male sterility that could be regulated to allow controlled male fertility for the propagation of the female line and genetically restored by the male parent to allow the production of selffertile hybrids.

DESCRIPTION OF INVENTION

It is an object of the invention as claimed herein, to provide a method for producing genic male sterility in plants. It is also an object of this invention to provide a method of producing genic male sterility which can be readily adapted to the production of hybrid seed, including hybrid seed with "restored" male fertility or male sterility which is not expressed in the plants grown from said seed.

For certain crops of interest, such as vegetables, it is only the leaves stems or roots of the plant that are sold commercially. Therefore, even though the male sterility trait may be inherited and expressed in the hybrid plant it is not necessary to overcome or restore male fertility in the seed of the hybrid plant. However, for other crops, the commodity of commerce is the seed or fruit produced by the hybrid plant. Thus for optimal commercial utility of the hybrid it is desirable that the hybrid is self-fertile.

In addition, the use of genic male sterile plants for commercial seed production requires the increase of seed of the genic male-sterile line (frequently called maintenance). Certain aspects of the invention as described herein, relate to the increase or maintenance of seed with genic male-sterility.

Specifically, it is an object of the present invention to provide a method of producing hybrid seed in three stages as follows:
 (a) producing a genetically transformed female parent by:
  i) inserting into the genome of a plant cell of said pollen producing plant which is capable of being regenerated into a differentiated whole plant, one or more recombinant DNA sequences comprising antisense DNA which block the production of functional pollen grains or render the developing pollen grains susceptible to a chemical agent or physiological stress which blocks the production of functional pollen grains;
  ii) obtaining a transformed plant cell of said plant; and
  iii) regenerating from said plant cell a plant which is genetically transformed with said DNA sequences described in (a)(i) above and which is male sterile or carries the male sterile trait,
 (b) increasing the number of female parent plants by:
  i) fertilizing the genetically transformed plant described in step (a) with pollen produced by a suitable male fertile plant, in a manner to effect a seed increase of genetically transformed plants; or
  ii) clonal propagation of said genetically transformed plant described in step (a) using tissue explants thereof, or other in vitro propagation techniques;
 (c) effecting a hybrid cross by pollinating said genetically transformed female parent plants with pollen produced by suitable male parent line.

According to one aspect of the present invention genic male sterility may be produced by transforming plant cells that are capable of regeneration into a differentiated whole plant, with a recombinant DNA molecule ("antisense DNA") that codes for RNA that is complimentary to and capable of hybridizing with the RNA encoded by a gene that is critical to pollen formation or function (the "sense gene"), thereby inhibiting the expression of the sense gene. The antisense DNA is preferably constructed by inverting the coding region of the sense gene relative to its normal presentation for transcription to allow for transcription of its complement, hence the complementariness of the respective RNAs encoded by these DNA's. In order to block the production of mRNA produced by the sense gene, the antisense DNA should preferably be expressed at approximately the same time as the sense gene. The timing must be approximate in the sense that the antisense RNA must be present within the cell to block the function of the RNA encoded by the sense gene. To accomplish this result, the coding region of the antisense DNA is preferably placed under the control of the same promoter as found in the sense gene thereby causing both to be transcribed at the same time. The concept of regulating gene expression using antisense RNA is described in Weintraub, H. et al., Antisense RNA as a molecular tool for genetic analysis, Reviews—Trends in Genetics, Vol. 1 (1) 1986.

Thus, according to one aspect of the invention as claimed herein, we provide a method of producing a male sterile plant from a plant selected from those species of pollen producing plants that are capable of being genetically transformed, which method comprises:
 (a) identifying and isolating, preferably from said pollen producing plant, a sense gene or coding sequence that is critical to pollen formation or function in said plant;

(b) inserting into the genome of a plant cell of said plant that is capable of being regenerated into a differentiated whole plant, a recombinant double stranded DNA molecule comprising:
  (i) a DNA sequence that codes for RNA that is complimentary to the RNA sequence encoded by said sense gene or coding sequence;
  (ii) a promoter which functions in said plant cell plant to cause transcription of said DNA sequence into RNA at about the time of transcription of said sense gene or coding sequence; and preferably
  (iii) a terminator sequence which defines a termination signal during transcription of said DNA sequence;

(c) obtaining a transformed plant cell of said plant; and (d) regenerating from said transformed plant cell a genetically transformed plant which is male sterile.

In accordance with the preceding method the invention is also directed to a totipotent plant cell which has been transformed with a recombinant DNA molecule as defined in step (b) and which is capable of being regenerated into a male sterile plant.

It is possible that the RNA transcribed from the antisense DNA will be effective in blocking translation of the RNA encoded by the sense gene even though a terminator sequence is not encoded by said recombinant DNA molecule comprising the antisense DNA.

According to another aspect of the preceding method as claimed in the claims, we provide a method of increasing the production of seed of the genic male sterile line by transforming the plant of interest with an antisense gene that is linked to a gene that confers resistance to a selective agent. According to this scheme, it is possible to produce a male sterile line by crossing the genetically transformed plant (male sterile) with a suitable non-transformed male fertile plant and using said selective agent to select for plants containing the antisense gene among plants grown from seed produced from such a cross. Theoretically, any effective selective agent for which a resistance gene has been identified could be used within the scope of this aspect of the invention, including but not limited to genes coding for resistance to herbicides and plant diseases. Such a selective agent could be said to fall within two broad non-mutually exclusive categories, a chemical agent and a physiological stress. A chemical agent, such as a herbicide, could be used to produce male sterile plants on a commercial scale. Examples of herbicides for which a resistance gene has been identified are glyphosate (described in Comai, L., Facciotti, D., Hiatt, W. R., Thompson, G., Rose, R. E., Stalker, D. M., 1985, Nature, Vol. 317, Pages 741-744) and chlorsulfuron (described in Haughn, G. W., and Somerville, C. R., 1986, Mol. Gen. Genet., Vol. 210, Pages 430-434).

Thus, according to another aspect of the invention as claimed herein, we provide a method of producing hybrid seed from plants selected from those species of pollen producing plants which are capable of being genetically transformed comprising the steps of:

(a) producing a genetically transformed plant which is made sterile by:
  i) identifying and isolating, preferably from said pollen producing plant, a sense gene or a coding sequence that is critical to pollen formation or function in said plant;
  ii) inserting into the genome of a plant cell of said plant that is capable of regeneration into a differentiated whole plant, a gene which confers on said plant resistance to a chemical agent or physiological stress and, linked to said gene, a gene comprising:
    (A) a DNA sequence that codes for RNA that is complimentary to the RNA sequence encoded by said sense gene or coding sequence;
    (B) a promoter which functions in said plant cell to cause transcription of said DNA sequence into RNA at about the time of transcription of the RNA encoded by said sense gene or coding sequence; and preferably;
    (C) a terminator sequence which defines a termination signal during transcription of said DNA sequence;
  iii) obtaining a transformed plant cell of the said plant; and
  iv) regenerating from said transformed plant cell a plant which is genetically transformed with the genes described in step (a) ii ) above; and (b) increasing the number of genetically transformed plants by:
  i) crossing the genetically transformed plant described in step (a) iv) above with suitable male fertile plant;
  ii) using the same chemical agent or physiological stress to eliminate plants which do not contain the genes described in step (a) ii) above among plants grown from seed produced by such cross; and
  iii) repeating such a cross over several generations with the plants obtained as in step (b) ii) above in the presence of said chemical agent or physiological stress to increase the numbers of male sterile plants;

(c) effecting a hybrid cross by pollinating said male sterile plants with pollen from suitable male fertile donors.

In accordance with the preceding method the invention is also directed to a cell totipotent plant which has been transformed with genes as defined in step (a) ii) sterile plant.

In a hybrid seed production scheme where there are alternating rows of male sterile plants and male fertile plants, it may be simpler but not essential to carry out the final selection of male steriles in the field alongside the male fertile donors. Therefore it is desirable if the suitable male fertile donors are previously transformed to resistance to the selective agent to avoid having to selectively apply said agent to the rows of male sterile plants. Therefore step (c) would be accomplished by growing seed produced from a cross between the selected genetically transformed plants and suitable male fertile donors, alongside seed of suitable male fertile donors which have previously been made resistant to said chemical agent or physiological stress (the selective agent).

In accordance with the preceding methods, the invention is also directed to a plant containing a recombinant DNA molecule which comprises:

(a) a DNA sequence that codes for RNA that is complimentary to the RNA sequence encoded by a sense gene that is critical to pollen formation or function in said plant;

(b) a promoter which functions in said plant to cause transcription of said DNA sequence into RNA that is at about the time of transcription of the RNA encoded by said sense gene; and preferably (c) a terminator sequence that defines a termination signal during transcription of said DNA sequence.

In accordance with the preceding methods the invention is also directed to hybrid seed containing a recombinant DNA molecule which comprises:

(a) a DNA sequence that codes for RNA that is complimentary to the RNA sequence encoded by a sense gene that is critical to pollen formation or function in a plant grown from said seed;

(b) a promoter which functions in a plant grown from said seed to cause transcription of said DNA sequence into RNA at about the time of transcription of the RNA encoded by said sense gene; and preferably (c) a terminator sequence that defines a termination signal during transcription of said DNA sequence.

According to another aspect of the invention as claimed herein, we regulate the expression of the coding region of the antisense DNA by using an inducible promoter. In this scheme, the promoter can be left in an induced state throughout pollen formation or at least for a period which spans the period of transcription of the sense gene. A promoter that is inducible by a simple chemical is particularly useful since the male sterile plant can easily be maintained by self-pollination when grown in the absence of said chemical. Restoration is inherent in growing plants produced from hybrid seed in the absence of said inducer.

Thus according to another aspect of the invention as claimed herein we provide a method of producing hybrid seed with restored fertility from plants selected from those species of pollen producing plants which are capable of being genetically transformed comprising the steps of:

(a) producing a genetically transformed plant which carries the male sterile trait by:
  i) identifying and isolating, preferably from said pollen producing plant, a sense gene that is critical to pollen formation or function in said plant;
  ii) inserting into the genome of a plant cell of said plant that is capable of regeneration into a differentiated whole plant, a recombinant double stranded DNA molecule comprising:
    (A) a DNA sequence that codes for RNA that is complimentary to the RNA sequence encoded by said sense gene or coding sequence;
    (B) an inducible promoter which can function in said plant cell to cause transcription of said DNA sequence into RNA during the time of transcription of said sense gene or coding sequence; and preferably
    (C) a terminator sequence which defines a termination signal during transcription of said DNA sequence
  iii) obtaining a transformed plant cell of said plant; and
  iv) regenerating from said transformed plant cell a plant which is genetically transformed with said double stranded DNA molecule described in (ii) above and can be rendered male sterile by said inducer;

(b) increasing the number of genetically transformed plants by growing the genetically transformed plant described in step (a)(iv) above in the absence of the relevant inducer to produce a male-fertile plant, permitting self-fertilization and growing seed of such a plant, over a number of generations, in the absence of the inducer to increase the number of genetically transformed plants;

(c) effecting a hybrid cross by growing said genetically transformed plants alongside plants of a suitable line of male fertile donors in the presence of the relevant inducer during pollen formation in order to produce male sterile plants and permit cross-pollination of said male sterile plants.

In accordance with the preceding method the invention is also directed to a totipotent plant cell which has been transformed with a recombinant DNA molecule as defined in step (a) (ii) above and which is capable of being regenerated into a plant which carries the male sterile trait.

In accordance with step (a) of the preceding method we provide a method to produce a plant which carries the male sterile trait.

In accordance with the preceding method, the invention is also directed to a plant which contains a recombinant DNA molecule comprising:

(a) a DNA sequence that codes for RNA that is complimentary to the RNA sequence encoded by a sense gene which is critical to pollen formation or function in said plant;

(b) an inducible promoter which functions in said plant to cause transcription of said DNA sequence into RNA during the time of transcription of said gene; and (c) a terminator sequence which defines a termination signal during transcription of said DNA sequence.

In accordance with the preceding method the invention is also directed to hybrid seed containing a recombinant DNA molecule which comprises:

(a) a DNA sequence that codes for RNA that is complimentary to the RNA sequence encoded by a sense gene which is critical to pollen formation or function in a plant grown from said seed;

(b) an inducible promoter which functions in said plant to cause transcription of said DNA sequence into RNA during the time of transcription of said sense gene; and (c) a terminator sequence which defines a termination signal during transcription of said DNA sequence.

According to another aspect of the invention as claimed herein, we provide a DNA coding sequence isolated from a plant of the species Brassica napus cv. Westar which is expressed only in microspores and whose expression is critical to microspore development. It is believed that this DNA fragment, the sequence of which is shown in FIGS. 2a–2c, (nucleotides 600–2430) will be found and expressed exclusively in pollen in other species of pollen-bearing plants, particularly species of plants within the genus Brassica and the family Cruciferae. The occurrence of this sequence in other species of pollenbearing plants may be routinely ascertained by known hybridization techniques. It is believed that the similarity of plant genes from species to species will allow for the preceding aspects of the present invention to be carried out using said DNA fragment in any number of pollen bearing plant species that are capable of being genetically transformed. The universality of plant genes has been widely documented in the literature and homologous plant genes have been described for plant actins (Shah, D. M., et al, J. Mol. Appl. Genet. 2:111–126, 1983), phytochrome (Hershey, H. P., et al., Proc. Natl. Acad. Sci. USA 81:2332–2337, 1984) storage proteins (Singh, N. K., et al., Plant Mol. Biol. 11:633–639,. 988) enzymes such as glutamine synthase (Lightfoot, D. A., et al, Plant Mol. Biol. 11:191–202, 1988, and references within) and nitrate reductase (Cheng, C., et al, EMBO Jour. 7:3309–3314). These and other examples in the literature clearly demonstrate that many plant genes are highly conserved. It is also clear that this conservation applies not only to structural proteins but to enzymatic proteins important to cellular physiology. Therefore, it is believed that said DNA fragment, when found in another plant species, will be critical to microspore development and will be able to be employed to carry out the present invention in such species. Furthermore, it is to be understood that any number of different genes that are crucial to microspore development or tissues uniquely involved in and critical to microspore development could be isolated and used in accordance with the preceding methods.

According to another aspect of the invention, we provide a pollen specific promoter sequence (nucleotide 1–595 shown in FIGS. 2a–2c) that can be utilized to limit the expression of any given DNA sequence to pollen tissue and to a period during pollen formation. The pollen specific promoter can be used to limit the expression of DNA sequences adjacent to it, to pollen tissue in both the Solanacae and Cruciferae families as provided for in the specific examples and it is fully believed that this DNA fragment or functional fragment thereof will function as a pollen specific promoter in all pollen bearing plant species of interest that are capable of being genetically transformed. This pollen specific promoter can be used in conjunction with its naturally flanking coding sequence described above (nucleotides 600–2430) or any other coding sequence that is critical to pollen formation or function to carry out each of the preceding aspects and embodiments of this invention which do not call for the use of an inducible promoter.

By using a pollen specific promoter to regulate the expression of the antisense DNA, it is possible to interfere with normal microspore development in any given plant, without having to first isolate from the genomic DNA of said plant, a gene which codes for a developmentally regulated protein that is critical to microspore development. We will describe a method to produce a male sterile plant where the sense gene targetted for inactivation is a gene that is critical to cellular function or development and is expressed in metabolically competent cell types. To produce a male sterile plant, such a gene is specifically inactivated in pollen by using a pollen specific promoter to limit the transcription of its antisense DNA complement to pollen tissue. We will also describe a method to produce a male-sterile plant, wherein the sense gene targeted for inactivation is a foreign gene which confers on the plant resistance to a chemical agent or a naturally occurring or artificially induced physiological stress. This gene can be inserted into the genome of the plant, prior to, after or concurrently with the antisense DNA. A male sterile plant can be produced by growing a plant in the presence of such a stress during pollen formation and using an antisense gene comprising said pollen specific promoter to specifically inactivate, in pollen, during pollen formation, a gene conferring on the remainder of the plant resistance to said stress. Any stress which can adequately be controlled on a large scale and for which a resistance gene has been identified may theoretically be employed in this scheme, including possibly but not limited to herbicides, pathogenic organisms, certain antibiotics and toxic drugs. In this scheme, a male sterile plant line can be maintained by self-pollination when grown in the absence of the biochemical or physiological stress. Restoration is inherent in growing plants produced from hybrid seed in the absence of said stress.

It is expected that one may use any number of different pollen specific promoters to carry out this invention. It is often difficult to determine a priori what pollen specific promoter could be used to inhibit a gene that is critical to pollen development or cellular function and development, but certain conditions must be met. The pollen specific promoter used to carry out the relevant aspects of this invention should be a promoter that functions to cause transcription of the antisense gene at a time concomitant with the expression of the sense gene sought to be inactivated. The pollen specific promoter should also function as to produce sufficient levels of antisense RNA such that the levels of the sense gene product are reduced. Investigations of the mechanism of antisense RNA inhibition of gene expression in model systems have suggested that equal or greater than equal levels of antisense RNA may be required in order to observe a significant reduction of sense gene activity. However, in some cases it is noted that low levels of antisense RNA can have a specific reduction in sense gene activity. Therefore it is suggested that the pollen specific promoter that is used to carry out certain aspects of this invention be chosen based on the observation that the pollen specific promoter functions to cause the expression of any sequences adjacent to it to be transcribed at a time that parallels or overlaps the period of time that the sense gene sought to be inactivated is express and that the levels of antisense RNA expressed from the antisense gene be of levels sufficient to inhibit the sense gene expression, usually to mean greater than or equal to the levels of sense RNA.

The determination of the most likely developmental stage in which the sense gene is targeted for inactivation can be accomplished by chosing a time in the developmental pattern of pollen formation at which the sense gene is maximally expressed and using a pollen specific promoter that displays a similar developmental pattern.

Thus according to another aspect of our invention, we provide a method of producing a male sterile plant from a plant selected from those species of pollen bearing plants that are capable of being genetically transformed which method comprises the steps of:

(a) identifying and isolating, preferably from said pollen producing plant, a sense gene or coding sequence that is critical to cellular function or development and expressed in metabolically competent cell types;

(b) inserting into the genome of a plant cell a recombinant double stranded DNA molecule comprising:
i) a DNA sequence that codes for RNA that is complimentary to the RNA encoded by said sense gene or coding sequence;
ii) a pollen specific promoter which functions in said plant cell to cause transcription of said DNA sequence into RNA in a time frame which enables said RNA to block the function of the RNA encoded by said sense gene or coding sequence; and preferably
iii) a terminator sequence which defines a termination signal during transcription of said DNA sequence;

(c) obtaining a plant cell that has been genetically transformed with said DNA sequence;
(d) regenerating from said transformed plant cell a genetically transformed plant which is male sterile.

In accordance with the preceding method the invention is also directed to a totipotent plant cell which has been transformed with a recombinant DNA molecule as defined in step (b) above and which is capable of being regenerated into a male sterile plant.

Similarly, in accordance with another aspect of this invention we provide a method of producing hybrid seed from plants selected from those species of pollen producing plants which are capable of being genetically transformed comprising the steps of:

(a) producing a male sterile plant by:
   i) identifying and isolating, preferably from said pollen producing plant, a sense gene or a coding sequence that is critical to cellular function or development and expressed in metabolically competent cell types;
   ii) inserting into the genome of a plant cell of said plant that is capable of regeneration into a differentiated whole plant, a gene which confers on said plant resistance to a chemical agent or physiological stress and, linked to said gene, a recombinant DNA sequence comprising:
      (A) a DNA sequence that codes for RNA that is complimentary to the RNA sequence encoded by said sense gene or coding sequence;
      (B) a promoter which functions in said plant cell to cause transcription of said DNA sequence into RNA in a time frame which enables said RNA to block the function of the RNA encoded by said sense gene or coding sequence; and preferably
      (C) a terminator sequence which defines a termination signal during transcription of said DNA sequence;
   iii) obtaining a transformed plant cell of said plant; and
   iv) regenerating from said transformed plant cell a plant which is genetically transformed with the genes described in step (a)(ii) above and which is male sterile; and
(b) increasing the number of genetically transformed plants by:
   i) crossing the genetically transformed plant described in step (a)(iv) above with a suitable male fertile plant;
   ii) using a chemical agent or physiological stress to eliminate plants which do not contain the genes described in step (a)(ii) above among plants grown from seed produced by such cross; and
   iii) repeating such a cross over several generations with the plants obtained as in step (b)(ii) above in the presence of said chemical agent or physiological stress to increase the numbers of male sterile plants;
(c) effecting a hybrid cross by pollinating said male sterile plants with pollen from a suitable male fertile donors.

In accordance with the preceding method the invention is also directed to a totipotent plant cell which has been transformed with a gene and a recombinant DNA sequence as defined in step (a) (ii) above and which is capable of being regenerated into a male sterile plant.

Again it is to be understood that where there are alternating rows of male sterile plants and male fertile plants, it may be simpler but not essential to carry out the final selection of male steriles in the field alongside the male fertile donors. Therefore it is desirable if the suitable male fertile donors are previously transformed to be resistant to the selective agent to avoid having to selectively apply said agent to the rows of male sterile plants.

Therefore, in accordance with the two preceding aspects of this invention, the invention is also directed to a plant and hybrid seed containing DNA comprising a recombinant DNA molecule which comprises:

(a) a DNA sequence that codes for RNA that is complimentary to mRNA encoded by a gene that is essential to cellular function or development in metabolically competent cell types;
(b) a pollen specific promoter which functions in said plant or plant grown from said hybrid seed to cause transcription of said DNA sequence into RNA in a time frame which enables said RNA to block the function of the RNA encoded by said gene; and preferably
(c) a terminator sequence which defines a termination signal during transcription of said DNA sequence.

It is to be understood that a sense gene that codes for a protein that is critical to cellular function or development may be identified in the literature and isolated in a simplified fashion according to the methods described below.

Examples of such proteins are proteins such as actin, tublin or ubiquitin, three proteins which are essential to cellular growth and development.

Sequences for actin genes isolated from plants have been published ( for example; Baird W. V., and Meagher, R. B., EMBO J. 6:3223–3231, 1987, or Shah, D. M., Hightower, R. C. and Meagher, R. B., Proc Natl Acad Sci USA 79: 1022–1026, 1982) and actin is known to play a critical role in normal cellular function especially during mitosis and meiosis where actin forms part of the cellular apparatus for cellular division.

The sequence for plant tubulin has also been described (Raha, D., Sen, K. and Biswas, B. B. Plant Mol Biol 9:565– 571, 1987). Tubulin, like actin, is known to be important in the cellular life cycle particularly in regards to cell shape, transport and spindle formation during mitosis and meiosis.

The DNA sequence for plant ubiquitin has also been published (Gausing, K. and Barkardottir, R. Eur J. Blochem 158:57–62, 1986). Ubiquitin is a protein involved in the turnover of cellular proteins and as such has a critical role in the regulation of specific cellular protein levels. In addition, ubiquitin is one of the most highly conserved proteins in eukaryotic cells. Interference with ubiquitin expression can cause abnormalities in the turnover of cellular proteins.

If any of the aforementioned proteins are not present in the cell, proper cellular function is interfered with and the cell fails to develop properly.

It is believed that a gene that is found to be essential to cellular growth or development in one plant species will have a similar counterpart in other plant species, since it is generally understood that within the plant kingdom there are genes that are nearly identical or very homologous involved in the basic processes that control or are a result of cellular development. It is further believed that a gene that interferes with the expression of said gene (i.e. an antisense gene) in one plant species will have the ability to do so in other plant species.

The similarity and universality of these genes have been exemplified in the literature. The tissue-specific and developmentally regulated expression of a wheat endosperm protein synthesized in tobacco plants genetically transformed with this wheat gene has been reported (Flavell, R. B., et al, Second International Congress for Plant Molecular Biology, Abstract #97). In that example, the wheat gene functioned in the tobacco plant in an identical fashion to the way in which it functions in a wheat plant. Other literature clearly shows that the regulation of a specific gene, which can be in many cases complex, is maintained in transgenic plants. One example of this is the phytochrome mediated regulation of a wheat Chlorophyll a/b-binding protein in transgenic tobacco (Nagy, F. et al, EMBO Jour. 5:1119–1124, 1986). In this example the light responsive specific regulation of the wheat gene was maintained in the foreign genetic environment. Not only do cereal genes function in a conserved manner, but genes from other plant species that are more closely related maintain functionality in heterologous genetic systems. Pea seed proteins are expressed properly in tobacco plants (Higgins, T. J. V., et al Plant Mol. Biol. 11:683–696, 1988), as are soybean seed proteins, (Barker, S. J., et al, Proc. Natl. Acad. Sci.USA 85:458–462, 1988) and pea rbcS genes (Nagy, F. et al., EMBO Jour. 4:3063–3068, 1985 ). The scientific literature has numerous other examples of genes that have been used to genetically transform plants and those genes maintain their ability to function properly in this new genetic environment. Therefore the conserved nature of these genes, not only in the DNA sequences which control the expression of these genes, but the actual protein structure coded for by these genes, is similar among the plant species.

It follows that one should be able to specifically inhibit the production of these proteins by using antisense DNA which is specific to the mRNAs encoded by the published sequences and a pollen specific promoter according to the methods described above.

According to another aspect of the invention as claimed herein, we provide a method of producing a male sterile plant from a plant selected from those species of pollen producing plants which are capable of being genetically transformed, which method comprises the steps of:

(a) transforming a plant cell of said plant which is capable of being regenerated into a differentiated whole plant with a sense gene which confers on said plant resistance to a chemical agent or a naturally occurring or artificially induced physiological or biochemical stress;

(b) regenerating from said transformed plant cell a genetically transformed plant which is resistant to the same stress;

(c) inserting into the genome of a plant cell of the stress resistant plant which is capable of being regenerated into a differentiated whole plant a recombinant double stranded DNA molecule comprising:

i) a DNA sequence that codes for RNA that is complimentary to the RNA sequence encoded by the said sense gene;

ii) a pollen specific promoter which functions in said plant cell to cause transcription of said DNA sequence into RNA; and preferably iii) a terminator sequence which defines a termination signal during transcription of said DNA sequence;

(d) obtaining a plant cell of said stress resistant plant which has been transformed with the gene described in step (c) above;

(e) regenerating from said transformed plant cell a plant which has been genetically transformed with the genes described in step (a) and step (c) above and can be rendered male sterile by said chemical agent or stress; and (f) growing said genetically transformed plant described in step (e) above in the presence of the same chemical agent or stress during pollen formation to produce a male sterile plant.

In accordance with the preceding method the invention is also directed to a totipotent plant cell which has been transformed with a recombinant DNA molecule as defined in step (c) above and which is capable of being regenerated into a plant which carries the male sterile trait.

It must be understood that the preceding aspect of our invention may also be accomplished by transforming a plant cell with both of the genes referred to in (a) and (c) above simultaneously, and therefore without an intermediate regeneration step (b).

In accordance with steps (a) through (e) of the preceding method, the invention is also directed to a method of producing a plant carrying the male sterile trait.

According to another aspect of the invention as claimed herein, we provide a method of producing hybrid seed with restored fertility from plants selected from those species of pollen producing plants which are capable of being genetically transformed comprising the steps of:

(a) producing a plant which carries a male sterile trait by:

i) inserting concomitantly or independently into the genome of a plant cell of said pollen producing plant which is capable of being regenerated into a differentiated whole plant, a sense gene which confers on said plant resistance to a chemical agent or a naturally occurring or artificially induced physiological stress and a recombinant double stranded DNA molecule comprising:

(A) a DNA sequence that codes for RNA that is complimentary to the RNA sequence encoded by said sense gene;

(B) a pollen specific promoter which functions in said plant cell to cause transcription of said DNA sequence into RNA; and preferably (C) a terminator sequence which defines termination signal during transcription of said DNA sequence;

ii) obtaining a plant cell of a plant which has been transformed with the genes described in step (i) above;

iii) regenerating from said transformed plant cell a plant which is genetically transformed with the genes described in step (i) above and can be rendered male sterile by said chemical agent or stress;

(b) increasing the number of genetically transformed plants:

i) growing the genetically transformed plant described in step (a) (iii) above in isolation from the same stress or chemical agent to produce a self-fertile plant;

ii) permitting self-fertilization; and iii) growing seed of such self-fertile plant, over a number of generations in isolation from the same stress or chemical agent to increase the number of genetically transformed plants;

(c) effecting a hybrid crossing growing said genetically transformed plants alongside plants of a suitable line of male fertile donors in the presence of the same stress or chemical agent during pollen formation to produce male sterile plant and to permit pollination of the male sterile plants.

In accordance with the preceding method the invention is also directed to a totipotent plant cell which has been transformed with a gene and a recombinant DNA molecule as defined in step (a) i) above and which is capable of being regenerated into a plant which carries the male sterile trait.

In accordance with the two preceding aspects of this invention, the invention is also directed to a plant comprising:

(A) a sense gene which confers on said plant resistance to a chemical agent or a naturally occurring or artificially induced physiological stress; and (B) a recombinant double stranded DNA molecule comprising:
  i) a DNA sequence that codes for RNA that is complimentary to the RNA sequence encoded by said sense gene;
  ii) a pollen specific promoter which functions in said plant to cause transcription of said DNA sequence into RNA; and
  iii) a terminator sequence which defines a termination signal during transcription of said DNA sequence, and hybrid seed containing DNA comprising:

(a) a sense gene which confers on a plant grown from said seed resistance to a chemical agent or a naturally occurring or artificially induced physiological stress; and (b) a recombinant double stranded DNA molecule comprising:
  i) a DNA sequence that codes for RNA that is complimentary to the RNA sequence encoded by said sense gene;
  ii) a pollen specific promoter which functions in said plant to cause transcription of said DNA sequence into RNA; and
  iii) a terminator sequence which defines a termination signal during transcription of said DNA sequence.

According to another aspect of the invention as provided in the claims, we describe a method of producing a male sterile plant by transforming a plant with a recombinant DNA molecule comprising a pollen specific promoter and a DNA sequence coding for a cytotoxic molecule. In theory, any toxic molecule which is known to be encoded by one or more identifiable DNA sequences may be employed within the scope of this aspect of the invention, including possibly but not limited to ricin and diphtheria toxin. We provide a method to produce hybrid seed with restored male fertility by crossing said male sterile plant with a suitable male fertile plant that has been transformed with a recombinant DNA molecule comprising the pollen specific promoter and a DNA sequence which is in the antisense orientation to that of the DNA sequence coding for the cytotoxic protein molecule, thereby inhibiting the expression in the hybrid plant of said DNA sequence coding for the cytotoxic molecule.

Thus according to another aspect of the invention as claimed herein we provide a method of producing a male sterile plant from a plant selected from those species of pollen producing plants which are capable of being genetically transformed, which method comprises the steps of:

(a) inserting into the genome of a plant cell of said plant a recombinant double stranded DNA molecule comprising:
  (i) a pollen specific promoter;
  (ii) a DNA sequence that codes for a cytotoxic molecule; and
  (iii) a terminator sequence which defines a termination signal during transcription of said DNA sequence;

(b) obtaining a transformed plant cell; and (c) regenerating from said transformed plant cell a genetically transformed plant which is male sterile.

In accordance with the preceding method the invention is also directed to a totipotent plant cell which has been transformed with a recombinant DNA molecule as defined in step (a) above and which is capable of being regenerated into a male sterile plant.

According to yet another aspect of the invention as claimed herein, we provide a method to produce hybrid seed with restored male fertility from plants selected from those species of pollen producing plants which are capable of being genetically transformed comprising the steps of:

(a) inserting into the genome of a plant cell of said pollen producing plant that is capable of being regenerated into a differentiated whole plant, a gene which confers on said plant resistance to a chemical agent or physiological stress and linked to said gene a recombinant double stranded DNA molecule comprising:
  (i) a DNA sequence which codes for a cytotoxic molecule;
  (ii) a pollen specific promoter which functions in said plant cell to cause transcription of said DNA sequence; and
  (iii) a terminator sequence which defines a termination signal during transcription of such DNA sequence;

(b) obtaining a transformed plant cell;

(c) regenerating from said plant cell a genetically transformed plant which is male sterile;

(d) increasing the number genetically transformed plants by:
  i) crossing the geneticaly transformed plant described in step (c) above with a suitable male fertile plant;
  ii) using a chemical agent or physiological stress to eliminate plants which do not contain the genes described in step (a) above among plants grown from seed produced by such cross; and
  iii) repeating such a cross over several generations with the plants obtained as in step (d) ii) above in the presence of said chemical agent or physiological stress to increase the numbers of male sterile plants;

(e) inserting into a plant cell of suitable male fertile plant selected from the same species a recombinant double stranded DNA molecule comprising:
  (i) a DNA sequence which codes for RNA that is complimentary to the RNA sequence coding for said cytotoxic molecule;

(ii) a promoter which causes transcription of the DNA sequence defined in step (d)(i) above at about the time of transcription of the DNA sequence defined in step (a) (i);

(iii) a terminator sequence which defines a termination signal during transcription of the DNA sequence described in step (e)(i) above;

(f) obtaining a transformed plant cell from step (d);

(g) regenerating from said transformed plant cell described in step (d) above a genetically transformed male fertile plant;

(h) producing a restorer line by permitting said genetically transformed male fertile plant to self fertilize and growing seed of such plant, over a number of generations to increase the numbers of genetically transformed male fertile plants;

(i) effecting a hybrid cross by pollinating said male sterile plants with pollen from said genetically transformed male fertile plants.

In accordance with the preceding method the invention is also directed to a totipotent plant cell which has been transformed with:

1) a gene and a recombinant DNA molecule as defined in step (a) and which is capable of being regenerated into a male sterile plant or 2) a recombinant DNA molecule as defined in step (e) above and which is capable of being regenerated into a male fertile plant carrying the restoration trait.

As discussed above, in a hybrid seed production scheme where there are alternating rows of male sterile plants and male fertile plants, it may be simpler but not essential to carry out the final selection of male steriles in the field alongside the male fertile donors. Therefore it is desirable if the suitable male fertile donors are previously transformed to resistance to the selective agent to avoid having to selectively apply said agent to the rows of male sterile plants.

In accordance with the preceding two aspects of the invention, the invention also contemplates a male sterile plant which has incorporated into its DNA a recombinant DNA molecule comprising:

(i) a DNA sequence which codes for a cytotoxic molecule;

(ii) a pollen specific promoter which functions in said plant cell to cause transcription of said DNA sequence;

(iii) a terminator sequence which defines a termination signal during transcripton of said DNA sequence;

and hybrid seed which has incorporated into its DNA said recombinant DNA molecule as well as another recombinant DNA molecule comprising:

(a) a DNA sequence which codes for RNA that is complimentary to an RNA sequence encoded by said gene coding for the cytotoxic molecule;

(b) a promoter which causes transcription of said DNA sequence into RNA at about the time of transcription of said gene coding for the cytotoxic molecule; and (c) a terminator sequence which defines a termination signal during transcription of said DNA sequence.

BRIEF DESCRIPTION OF THE DRAWINGS

FIGS. 2a, 2b and 2c are the nucleotide sequence of a portion of the clone L 4 represented in FIG. 1a.

FIGS. 2d and 2e are the nucleotide sequence of a portion of the clone L 19 shown in FIG. 1b.

DETAILED DESCRIPTION OF THE DRAWINGS

Figure 1A:
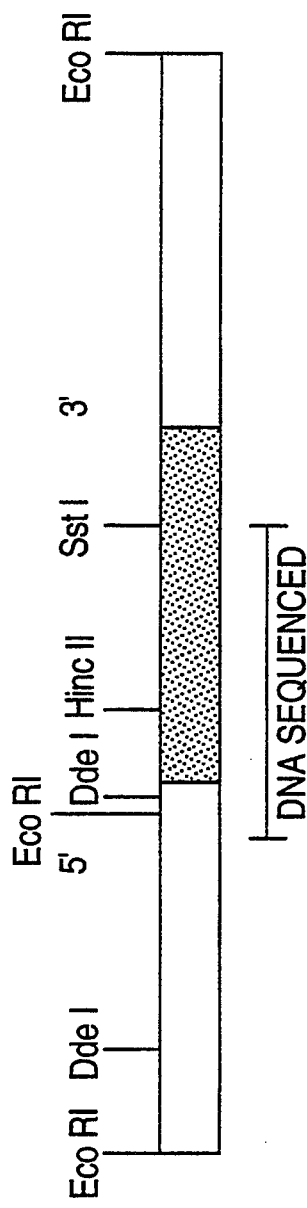
FIG. 1a is a schematic representation of a restriction map of L 4 a microspore specific genomic clone isolated from a Brassica napus genomic library.
Figure 1B:
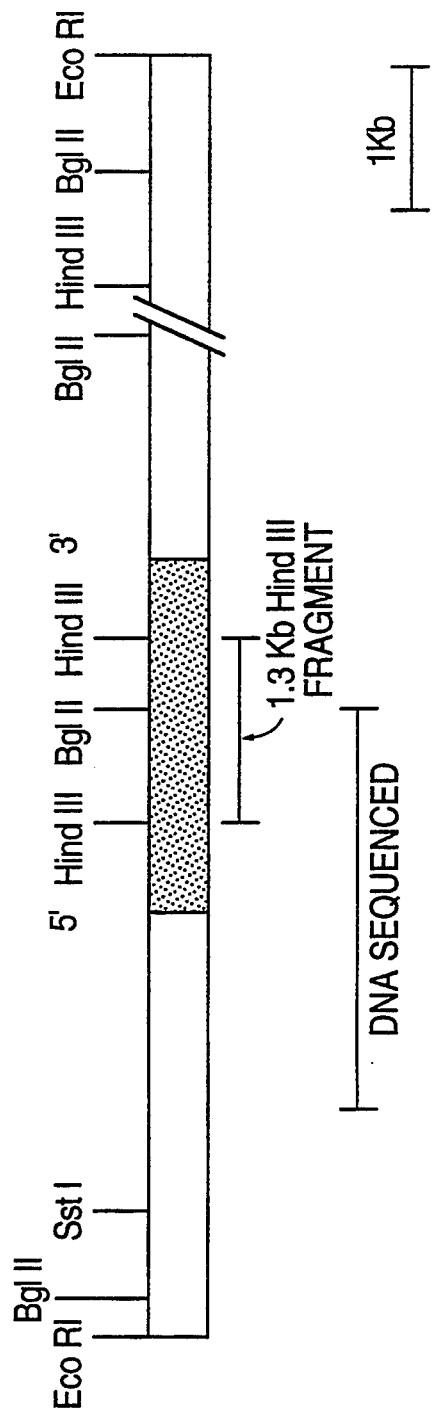
FIG. 1b is a schematic representation of a restriction map of L 19, a microspore specific clone isolated from a Brassica napus genomic library.

In FIGS. 1a and 1b, the orientation of the restriction maps of the microspore specific Brassica napus genomic clones L 4 and L 19 is from 5' to 3'. Clone L 4 was used for the isolation of a microspore specific promoter and for isolation of microspore specific gene coding fragments. Clone L 19 was used as a source for a microspore specific gene coding region. The 5' of each clone region contains the promoter region of the clone. The shaded region of each clone demarcates the approximate coding region of the clone. Only those restriction sites which are relevant to the constructions detailed below are shown. The right and left arms of the lambda cloning vector are not shown. Indicated below each clone is the region of DNA that has been sequenced. Those sequences are given in FIGS. 2a-2c and 2d-2e.

In FIGS. 2a-2c and 2d-2e the DNA sequence of selected portions of clones L 4 and L 19, respectively, are shown. Specifically, the sequences of the double stranded DNA in the regions indicated in FIGS. 1a and 1b are shown in the 5' to 3' orientation. For clone L 4, nucleotide 1 is 599 base pairs in front of the ATG codon of the coding region shown in FIG. 1a, the start of transcription is at nucleotide 526 and the start of translation is at nucleotide 600-603 (ATG). A Dde I site is shown at position 590 immediately upstream of the ATG start codon. This Dde I site and a further Dde I site shown 1900 nucleotides upstream of this site were used to excise the promoter region for the construction of PAL 1107. In addition, the position of the first two introns and exons are indicated. The precise start site of the third exon is not identified, only the approximate splice site is demarcated by the dashed line. The 3' termination site of the gene is 3' to the last nucleotide shown in this DNA sequence. The sequence of clone L 19 extends approximately 1.5 Kb from the leftmost Eco RI site to approximately the Bgl II site in the coding region. A Hind III site is shown at position 1899-1905. This site corresponds to the left most Hind III site in clone L 19.

Figure 3:
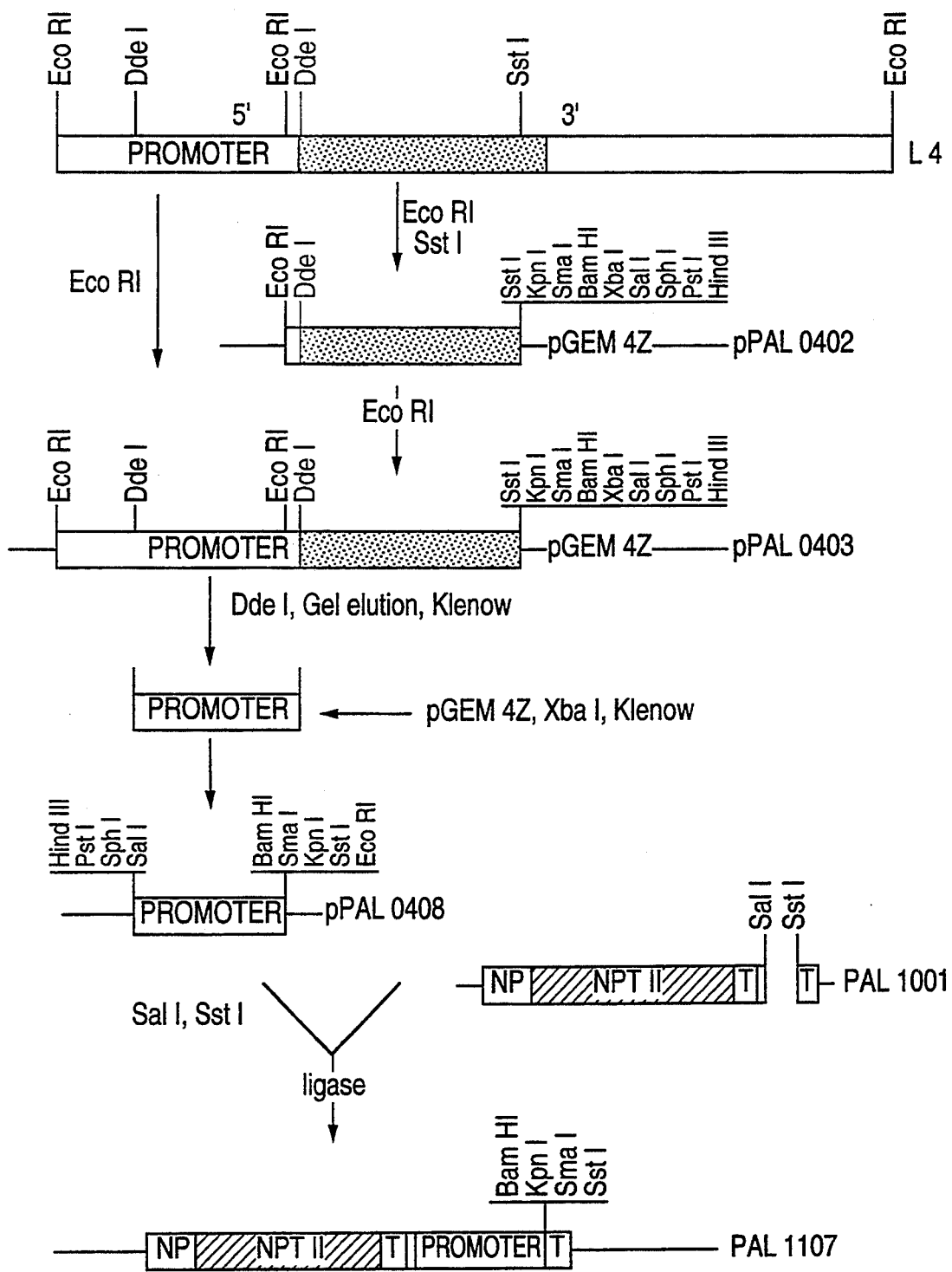
FIG. 3 is a schematic representation of a protocol for producing the vector PAL Example 1107, discussed in greater detail below.

In FIG. 3 the protocol for constructing PAL 1107 is shown. For this construction, the Eco RI - Sst I fragment that encompasses most of the coding region and 230 bases of the promoter region is subcloned into the plasmid vector pGEM 4Z using the Eco RI and Sst I sites in the polylinker region. This clone (pPAL 0402) is digested with EC©RI and the 2.5 Kb ECo RI fragment upstream of the coding region from the genomic clone L 4 is added, giving the clone pPAL 0403 with a reconstructed 5' region of clone L 4. The Dde I fragment is then isolated from pPAL 0403 by gel elution, made blunt with Klenow, and cloned into pGEM 4Z previously cut with Xba I and blunted with Klenow, creating pPAL 0408. pPAL 0408 is cut with Sal I and Sst I and the promoter fragment now containing a portion of the polylinker from pGEM 4Z is then cloned into PAL 1001 previously cut with Sal I and Sst I, creating PAL 1107. The vector contains the NPT II gene for selection in plant cells, plus the promoter region from the pollen specific clone L 4 followed by a portion of the polylinker from pGEM 4Z containing these unique sites for insertion of DNA fragments to be transcribed using the following restriction enzymes: Bam HI, Kpn I, Sma I and Sst I. The promoter region indicated is the promoter region of clone L 4, oriented in the 5' to 3' direction. DNA fragments placed at the 3' end of this fragment will be transcribed only in pollen. T represents the 260 bp Sst I - Eco RI restriction fragment containing the hopaline synthase polyadenylation signal.

Figure 4:
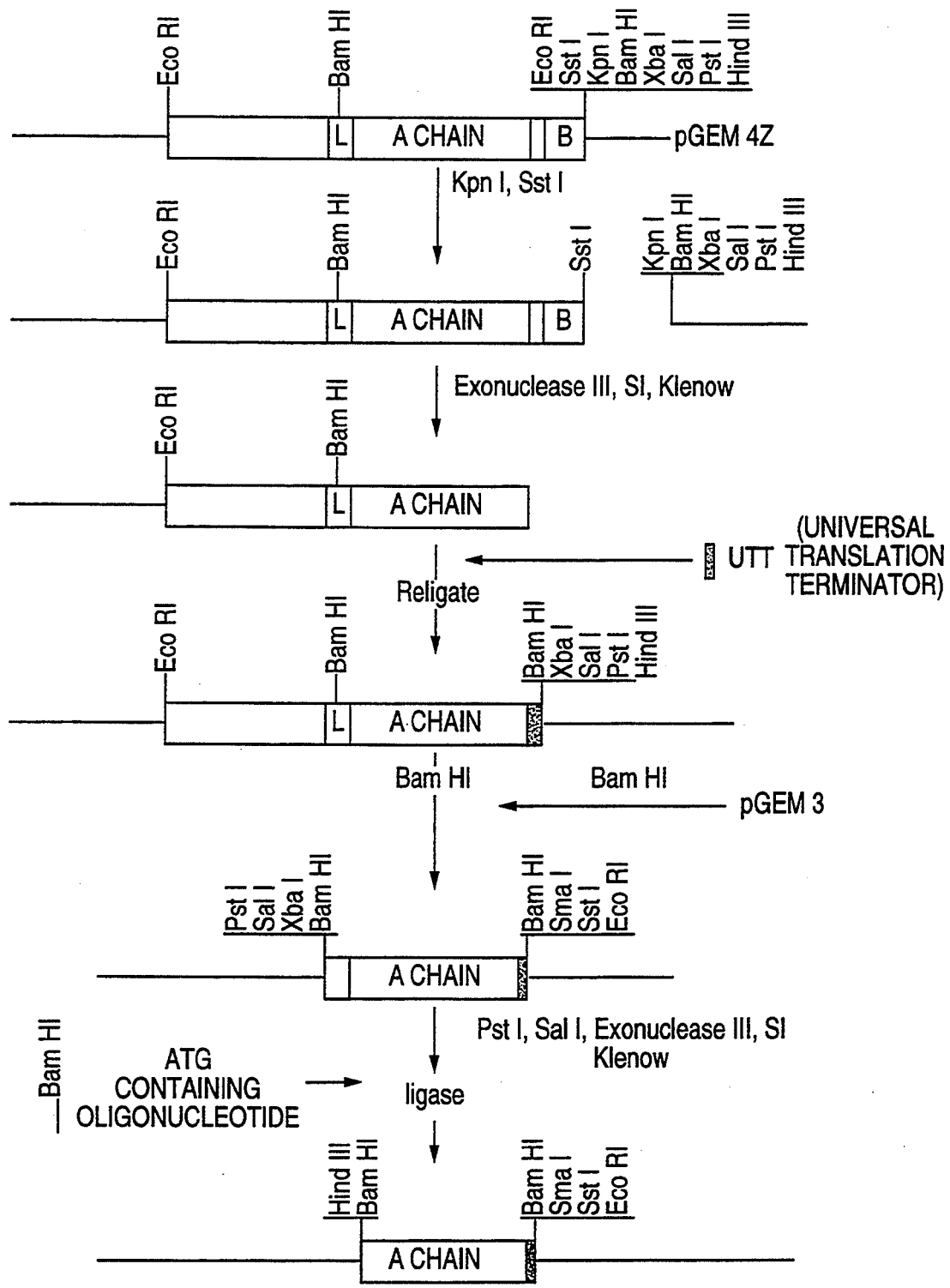
FIG. 4 is a schematic representation of a protocol for producing a clone containing a coding region of the A chain of the ricin gene.

In FIG. 4 the protocol for isolating Ricin A chain sequences is shown. A clone containing part of the ricin gene is isolated as a Eco RI fragment in pGEM 4Z as shown. The clone is digested with Kpn I and Sst I and digested with exonuclease III. Following SI digestion and blunt end repair by Klenow, the clone is religated in the presence of a universal translation terminator (purchased from Pharmacia P.L. Biochemicals). A clone containing this terminator and which was deleted to amino acid residue 262 of the A chain is recovered. This clone is digested with Barn HI and recloned into Barn HI cut pGEM 3 and a clone containing the orientation shown is chosen. The resultant clone is cut with Pst I and Sal I, then digested with exonuclease III followed by SI and Klenow treatment to make the DNA blunt ended. A palindromic linker that contains an ATG start codon and a site for Bam HI is added and the clone religated so that a Bam HI site was introduced before the ATG start. Clones are chosen, sequenced and one in which the ATG is in frame with the rest of the A chain coding sequence is chosen. This construction allows the ricin A chain sequence to be excised as Barn HI fragment. L represents the leader sequence for ricin whereas B represents a portion of the B chain of ricin.

DETAILED DESCRIPTION OF PREFERRED EMBODIMENTS

It is known that there are currently a limited number of species of plants that are capable of being transformed. Routine transformation is largely restricted to two plant families: Solanacae and Cruciferae. Examples of species included within these families are *Nicotiana tabacum* (Solanacae), *Lycopersicon esculentum* (Solanacae) and *Brassica napus* (Cruciferae). These include canola, tobacco and tomato plants. It is believed that the present invention may be carried out with plants selected from any one of said species. Furthermore, it is fully expected that the present invention may be carried out with any other species of plant that is later determined to be capable of being genetically transformed.

The pollen specific promoter referred to above was isolated from a plant of the species *Brassica napus.* It is believed, in respect of each of the species of plants enumerated in the preceding paragraph, each of which was transformed with a gene comprising said promoter, that it is possible to use said promoter to limit the expression of a given structural gene sequence to microspores and to a period during pollen formation. Current published scientific literature has clearly demonstrated that plant genes are universal and specifically that plant tissue-specific promoter fragments retain their function in other species. For example, wheat endosperm promoter fragments (Simpson, J., et al, EMBO Jour. 4:2723–2729, 1985), or the Alcohol Dehydrogenase (ADH) promoter fragments (Ellis, J. G., et al, EMBO Jour. 6:11–16, can function properly in other plant species genetically transformed with said promoter fragments. Accordingly, it is fully expected that the pollen specific promoter that we have isolated is capable of being utilized to limit the expression of any given structural gene sequence to microspores and to a period during pollen formation, in any other pollen-producing plant species of interest that is later found to be capable to being genetically transformed, including preferably species within the families Solanacae and Cruciferae and more preferably species of plants selected from the genus Brassica.

According to the present invention, the following advantages are achieved over other hybridization systems:

(a) Hybrid seed production is not labour intensive and can be achieved on a large scale with commercially acceptable costs;

(b) Male sterility is simply inherited and stable in response to environmental stresses that limit the effectiveness of self-incompatibility and CMS based schemes. Seed that is produced will be relatively uncontaminated by selfed seed;

(c) The system avoids the use of defective cytoplasmic organelles that may themselves detract from the performance of the hybrid seed; and (d) The system will greatly speed the development and increase the number of lines that can be tested as hybrid parents because it can be imposed on any inbred plant line capable of regeneration into transformed plants without the inclusion of additional genomic DNA. Additionally, plant lines can be tested for combining ability before incorporation of the hybridization system.

The schemes in which male fertility is controlled by controlling the presence of an inducer or a physiological stress are particularly advantageous for hybrid seed production on a large scale since propagation of the male sterile line can be accomplished by a simple means.

As a preferred embodiment of several aspects of our invention discussed above, we provide methods of introducing genic male sterility into a plant species of the genus Brassica, in respect of which a satisfactory CMS system is not available. These methods overcome the difficulties associated with the use of a CMS based male sterility system, specifically with regard to yield loss associated with defective mitochondria.

The following terms and expressions, when used throughout the disclosure and claims herein, are to be interpreted in accordance with the definitions set out below unless the context dictates that said terms and expressions are not to be so limited:

Antisense DNA—A DNA sequence produced when the sense DNA is inverted relative to its normal presentation for transcription and inserted downstream from a promoter.

The antisense DNA may be constructed in a number of different ways, provided that it is capable of being transcribed into RNA which is complimentary to and capable of blocking translation of the RNA produced by the sense gene.

Antisense RNA—RNA that is encoded by antisense DNA.

Capable of Being Gentically Transformed—In reference to a plant, this expression means a plant containing cells which can stably incorporate recombinant DNA molecule and be regenerated into a differentiated whole plant.

Critical to Pollen Formation or Function—Any gene that is specifically required for the development or function of pollen. Such genes include but are not necessarily limited to genes which are critical to microspore growth and development or microspore function (e.g. ability to germinate and effect fertilization) and genes which are critical and required for growth and developing of all cells and tissues associated with developing microspores such as the filament, taperum and the anther wall.

Gene—Structural gene with flanking expression signals or sequences.

Gene That Is Critical To Cellular Function Or Development—Any gene that codes for a product that is essential for the continued function or development of all metabolically competent cells such as but not limited to genes involved in essential cellular structures, essential bio-synthesis and essential metabolism.

Genomic DNA—The DNA of the plant genome.

Genomic Library—A collection of segments of genomic DNA which have been individually inserted into phage vectors, which collection is used to isolate specific genomic sequences.

Hybrid Plant—A plant grown from hybrid seed.

Hybrid Seed—Any seed produced by the cross-pollination of any particular plant inbred line by a pollen other than the pollen of that particular plant variety inbred line.

Microspore—A spore that develops into a pollen grain. This term is used interchangeably with "pollen".

Pollen Grain (or Pollen)—A structure derived from the microspore of seed plants that develops into the male gametophyte.

Pollen Specific Promoter—A promoter that functions exclusively in pollen.

Promoter—A DNA sequence (expression signal) that causes the initiation of transcription of sequences adjacent to it.

Restriction Fragment—A specific length fragment of DNA produced by the complete restriction digest of a particular DNA using the specified restriction digest.

Sense Gene—A DNA sequence that is capable of producing a functional protein product, which sequence consists of a promoter, a structural gene and a terminator. In the context of the present invention, we shall refer to the structural gene sought to be inactivated when combined with promoter and terminator sequences as a sense gene.

Sense RNA—RNA that is the normal product of transcription of a sense gene and therefore capable of being translated in vitro into a functional protein product.

Structural Gene—A DNA sequence that codes for a protein sequence.

Suitable Male Fertile Plant—Suitability for the purpose of producing hybrid seed is determined by standard crossing of different varieties with subsequent analysis of the progeny and selection of a variety with a superior combining ability. Suitability of a male fertile plant for the purpose of crossing with a male sterile plant to increase the number of male sterile plants means use of, but is not necessarily limited to use of, a plant of the same inbred line from which the male sterile plant is derived. In some instances the desired increase in plants that function as the male sterile female parent can be produced simply by selfing thus the suitable male fertile plant can also be itself.

Terminator—A DNA sequence (expression signal) that directs the end point of transcription in plants.

Transformation—The use of Agrobacterium sp. or any other suitable vector system(s) to transfer foreign DNA in a stable fashion into the genomic DNA of a plant species.

METHODOLOGY

In the foregoing description of the invention, we set forth, in general terms, the steps that can be employed to produce male sterile plants and hybrid seed in accordance with our invention. It is to be understood that these various steps may be accomplished by a variety of different procedures. In the following description of preferred procedures, we refer to several alternative procedures to accomplish these steps. However, it is contemplated that other variations will be apparent to those skilled in the art. Accordingly, the scope of the present invention is intended to be limited only by the scope of the appended claims.

The isolation of genes that are critical to pollen formation may be accomplished by a variety of procedures. In accordance with one aspect of the method of our invention, we identify by known methods, genes that are only expressed at specific stages during pollen development whose regulation is tightly controlled. The genes may be isolated by cloning techniques in accordance with the detailed method set out below. The isolation step may also be accomplished by ascertaining, according to standard cloning techniques discussed below, whether a given gene which is known to be critical to pollen formation and expressed exclusively in microspore tissue in one plant, has the same utility in another plant. It is also known that certain genes are critical to cellular function and are expressed in all cell types. These genes may be isolated using the published DNA sequences for these essential genes, some of which are conserved amongst the plant and animal species, and in conjunction with a promoter that limits gene expression to only pollen tissue be used for the construction of an antisense RNA gene that caused male sterility.

The antisense genes may be constructed according to any one of a variety of known methods. The preferred method of construction detailed below is to excise the double stranded coding region of the sense gene or a functional fragment thereof and to insert said double stranded DNA molecule downstream from a promoter, in an inverted orientation relative to its normal presentation for transcription. A terminator structure is preferably added to the end of this antisense gene. It is possible within the scope of the present invention to synthetically produce said antisense DNA sequence or a functional fragment thereof, according to known methods, and insert said sequence by known methods downstream from a promoter that will cause timely transcription of same into sufficient quantities of RNA.

The antisense gene may be introduced into the plant cell by any one of a variety of known methods preferably by first inserting said gene into a suitable vector and then using said vector to introduce said gene into a plant cell. The transformed plant cell is selected for by the presence of a marker gene for any one of a variety of selectable agents which is capable of conferring resistance to transformed plant cells to same agent. Transformed plant cells thus selected for can be induced to differentiate into mature plant structures. Additionally, it is to be understood that whereas some aspects of this invention may require the transformation of a plant cell with two different genes, that these genes may be physically linked by both being contained on the same vector or physically seperate on different vectors. It is also understood that if the genes are on different vectors, that the transformation of a plant cell can take place with both vectors simultaneously providing each vector has a unique selectable marker. Alternatively, the transformation of a plant cell with the two vectors can be accomplished by an intermediate regeneration step after transformation with the first vector.

Where the cost is warranted, and maintenance cannot be readily accomplished as discussed above, transformed plant cells can be grown in culture according to routine methodology to produce a cell line comprising a large number of transformed cells. A large number of transformed plants can be regenerated according to routine methodology from said transformed plant cell line to increase and maintain the male sterile line. Routine methodology for culturing such cells and regenerating transformed plants from such cells is described in such plant tissue culture hand books as: *Plant Tissue and Cell Culture,* C. E. Green, D. A. Somers, W. P. Hackett and D. D. Biesboer, Eds., Alan R. Liss, Inc., New York, *Experiments in Plant Tissue Culture,* Dodds, J. H. and Roberts, L. W. Eds., 1985, Cambridge University Press, or *Cell Structure and Somatic Cell Genetics of Plants,* Vasil, I. K., Ed., 1984, Academic Press, *Handbook of Plant Cell Culture, Volume 4, Techniques and Applications,* Evans, D. A., Sharp, W. R., and Ammirato, P. V., Eds., 1986, Macmillan Publishing Company.

It is also possible to produce male sterile plants by fusing cells of the transformed plant cell line with cells of plant species that cannot be transformed by standard methods. A fusion plant cell line is obtained which carries a genetic component from both plant cells. The fusion cells can be selected for cells that carry the antisense gene and in many cases induced to regenerate into mature plants that carry the male sterile trait.

It is to be understood that any one of a number of different promoters can be used to regulate the expression of the antisense gene, provided that the promoter causes transcription of said antisense gene at the proper time and into sufficient quantities of RNA to block the function of the sense RNA and thereby prevent its translation into protein required for proper microspore development. Complete inhibition of the expression of these genes is not needed, only expression that is reduced to the point that normal pollen development is interfered with. It is possible to use a combination of different genes and promoter structures to interfere with normal pollen development. A promoter or a method which could be used to amplify the expression of the antisense gene could be useful to ensure adequate production of antisense RNA.

When using a pollen specific promoter to inactivate a sense gene that is critical to pollen formation or function or to cellular growth or development, we discussed that it is often difficult to determine, a priori, what pollen specific promoter will effectively block the function of that gene. We discussed that it is preferable to use a pollen specific promoter that displays a similar developmental pattern to that gene. A convenient method to determine when the sense gene sought to be inactivated is expressed is to isolate RNA from developing microspores at different stages and to analyze this RNA for the expression of the sense gene by the so-called Northern analysis. This process will allow for the determination of the exact developmental period in which the sense gene is expressed. In order to determine the period in pollen development in which the pollen specific promoter sought to be used to activate said sense gene is expressed, a similar series of analysis can be carried out using as a probe for the expression of said pollen specific promoter a reporter gene joined to said promoter or the naturally occurring sense gene under the control of the pollen specific promoter found in the plant originally used for the isolation of the sense gene. When the pollen specific promoter is isolated from one plant and used in a different plant species the preferred method is the use of a reporter gene joined to said promoter to determine the exact developmental timing that that promoter fragment has in that particular plant species.

It is also to be understood that the antisense DNA does not necessarily have to code for RNA that is complimentary to the entire mRNA chain encoded by the sense gene provided that the mRNA encoded by the antisense gene is otherwise capable of hybridizing with and blocking translation of the native mRNA species targeted for inactivation. Accordingly the term antisense DNA when used in disclosure claims herein encompasses a functional fragment thereof.

A. Isolation of Genes that are Critical to Proper Development of Microspores To isolate genes that are specifically expressed in developing microspores, a genomic library of plant DNA may be constructed from DNA isolated from fresh young leaf material according to standard methodology, described in *Molecular Cloning, a Laboratory Manual* (Maniatis, T. Fritsch, E. F., and Sambrooks, J., Cold Spring Harbour Laboratory, Cold Spring Harbour, N.Y., 1982) and screened with probes derived from several tissues, one of which is made from microspore RNA. The other probes should be made from RNA from different tissues so as to represent genes expressed in tissues of the plant that would not be expected to include genes that are expressed in microspores. Examples of these would include but are not limited to such tissues as leaf, roots, seeds, stigma, stem and other plant organs. However, some genes will be expressed in all tissues. By surveying many plant tissues, it is possible to isolate genes expressed exclusively in microspores.

The microspore RNA may be isolated from microspores that are at the early to late uninucleate stage. Though it is possible to use other microspore stages certain difficulties might be confronted. The use of premeiotic stage microspores could prove to be problematic in many plant species since in some plants the callose wall has not formed yet and isolation of the immature microspores is technically difficult. Microspores that are isolated at the stages post nuclear division may have limited nuclear gene activity when compared to earlier stages. Therefore, the early to late uninucleate stages are preferred.

The microspores may be conveniently isolated from the anthers by manual dissection of the buds from the growing plant and subsequent removal of the anthers. Microspores are isolated from the anthers by gentle grinding of the anthers in a mortar and pestle in the presence of a solution of 10% sucrose. The extract is then filtered through a 44 um nylon mesh and the microspores are collected from the filtrate by centrifugation at 3000 x g for one minute. The pelleted microspores are resuspended in 10% sucrose, filtered and pelleted as before. Other methods of isolation can also be used to obtain microspores.

Tissues other than microspores can be disrupted by a variety of methods and the disrupted tissue can be used for RNA extraction. It is convenient to disrupt the tissue by using a motor driven homogenizer with 10 mls of a solution of 6M guanidinium-HCl, 0.1M Na acetate, pH 6.0, 0.1M beta-mercaptoethanol per gram of tissue. The homogenate is centrifuged at 5000 x g and the cleared supernatant is layered over a solution of 6M CsCl in Tris-EDTA buffer (TE buffer). Centrifugation at 100,000 x g for 12-20 hours at 15° C. is used to pellet the RNA which is subsequently resuspended in water and reprecipitated in the presence of 0.3M Na acetate and 2 volumes of ethanol. RNA is recovered by centrifugation and resuspended in water. The RNA obtained from such method can be fractionated by oligo-d-T cellulose chromatography to separate the polyadenylated mRNA from the bulk of the non-polyadenylated RNA. The microspore RNA is conveniently isolated by using a tight fitting motor driven glass homogenizer to disrupt the microspores. The homogenization of the microspores, 1 ml of a solution of 6M guanidinium-HCl, 0.1M Na acetate, pH 6.0, 0.1M beta-mercaptoethanol per 300 ul of packed microspores used as a RNA extraction buffer during the disruption of the microspores. The homogenate is centrifuged at 5000 x g and the cleared supernatant is layered over a solution of 6M CsCl in TE buffer. An overnight centrifugation at 100,000 x g is used to pellet the RNA which is subsequently resuspended in water and reprecipitated in the presence of 0.3M Na acetate and 2 volumes of ethanol. Other methods of RNA extraction can be used to obtain the RNA from the tissues described. Standard methodology using oligo-dT cellulose is used to obtain polyadenylated mRNA from these total RNA preparations.

The mRNA is labelled for the purpose of detection. It is convenient to make radioactive cDNA by using said mRNA and AMV reverse transcriptase in the presence of random hexanucleotide primers and alpha-[$^{32}$P]-dCTP. Probes are used for hybridization to nitrocellulose plaque lifts of plates containing the clones of the genomic library. Clones that can be identified as strongly hybridizing only to microspore cDNA and not cDNA from any other tissue examined are chosen. These clones are plaque purified and grown for DNA isolation. Alternative techniques for manipulating DNA and RNA as well as recombinant DNA, growing and isolating clones can be found in standard laboratory manuals, such as *Molecular Cloning, A Laboratory Manual* (Maniatis, T., Fritsch, E. F., and Sambrook, J. Cold Spring Harbour Laboratory, Cold Spring Harbour, N.Y., 1982 ).

In the case where the genomic DNA sequence of L 4 or L 19 from *Brassica napus* are used to carry out certain aspects of this invention, the preferred method to obtain ("isolate") a sense gene that is critical to pollen formation or function is to synthetically produce a homologous DNA sequence according to standard methodology (see for example Gait, M. J. (1984) in Oligonucleotide synthesis, a practical approach Gait, M. J. ed., pp 1–22, IRL Press, Oxford, U.K.), label said sequence for the purpose of detection and use said labelled sequence to screen a Brassica napus genomic library produced according to the methods described.

B. Construction of Antisense Genes

The identity of the promoter and coding region of a given genomic clone is determined by restriction mapping and hybridization analysis. This may be accomplished by hybridization of cDNA probes made from microspore RNA with restriction fragments of said DNA clones immobilized on nitrocellulose. Restriction endonuclease fragments which contain both the coding region and the regions of DNA on either side of the coding region are isolated by sub-cloning in the appropriate vectors. Once isolated, it is convenient to use techniques such as SI mapping and DNA sequencing to obtain exact coding regions and restrictions sites within the subcloned DNA. This analysis is easily accomplished once the polarity with respect to gene transcription is known.

In order to determine the polarity of transcription of the sense gene individual restriction fragments may be subcloned in commercially available vectors such as pGEM3, pGEM4, or pGEM3Z, pGEM4Z ( available from Promega Biotech, Madison, Wis., U.S.A. ). By using these vectors one is able to generate single stranded RNA probes which are complimentary to one or the other strands of the DNA duplex in a given subclone. These strand specific probes are hybridized to mRNA, in order to establish the polarity of transcription. Among these probes, one can isolate those probes which hybridize with and hence are complimentary to the mRNA. Using this information it is possible to clearly determine from what DNA strand of the double strand genomic DNA molecule the sense mRNA has been transcribed.

In order to isolate promoter DNA sequences from the coding region, the pGEM series of vectors can be used for the unidirectional deletion of sequences from the individual subclones. Additionally, transcriptional start sites of promoter regions may be mapped. This may be conveniently accomplished by using a single stranded RNA probe transcribed from the individual subclones in hybridization-protection experiments. Detailed descriptions of these experimental protocols can be found in a number of laboratory handbooks and in the manufacturer's technical notes supplied with the pGEM series of vectors. These experiments will clearly establish the promoter and coding regions of the pollen specific genomic clones.

The sequence of individual deletions in the pGEM vectors can be determined by didoexy sequencing of plasmid minipreps as described in the manufacturer's technical notes. Deletion subclones that are deleted to very near the start of transcription or specific restriction fragments that encompass the promoter region or the promoter region and start of transcription are chosen for the construction of genes that are expressed only in developing microspores of pollen bearing plants. Usually the promoter fragment is inserted upstream of a terminator such as the nos terminator found in pRAJ-221 (available from Clonetech Laboratories, Palo Alto, Calif.) and specific restriction fragments which are to be transcribed into antisense RNA are inserted between the promoter and terminator sequences. The entire construct is verified by combination of sequencing and restriction digests. The antisense gene thus constructed and verified may be inserted in T-DNA based vectors for plant cell transformation. T-DNA vectors that contain a selectable marker are preferred. It is to be understood that the antisense gene can be constructed in a variety of ways depending on the choice of vectors, restriction enzymes and the individual genes used. For example, it may be convenient as demonstrated by Example 1, to insert restriction fragments intended to be transcribed into antisense RNA into a T-DNA based vector to which a promoter and terminator structure have been previously added. Alternatively, it is possible to insert a promoter fragment upstream of a coding region and terminator that has been previously added to a T-DNA based vector. In addition, it may be desirable in some crops not to insert the antisense gene into a T-DNA based vector but rather into a vector suitable for direct DNA uptake. Promoters other than microspore specific promoters can be used and joined with specific restriction fragments of genes and terminators provided that these promoters function in microspores.

C. Transformation of Plant Cells

A number of published articles have dealt with the subject of plant transformation. Generally speaking, two types of methodology exist for transformation of plant cells: (1) use of an infectious agent such as Agrobacterium or viruses to deliver foreign DNA to plant cells, and (2) mechanical means such as naked DNA uptake or electroporation. In both cases, the desired result is the uptake of foreign DNA into the plant cell and subsequent stable integration of the foreign DNA into the nuclear genetic component of the plant cell. In the ensuing examples, we describe a particular type of methodology that may be used to produce transformed plants. However, it is to be understood that other methods can be used for the purpose of production of transformed plants containing antisense genes. These include but are not limited to: protoplast transformation, transformation of microspores, whole plant wounding with Agrobacterium followed by recovery of and regeneration from infected tissue, naked DNA uptake with Agrobacterium delivery systems and other methods such as electroporation.

D. Regeneration of plants from Transformed Plant Cells

After transformation of a plant cell, the plant cell is allowed to grow and develop into a whole plant. Usually this takes place over a period of time during which time selection of the transformed plant cells is accomplished by the application of a selective pressure such as an antibiotic, drug or metabolites that are toxic to the plant cell. Resistance to the selective pressure is conferred on the plant cell by the presence of a resistance gene on the transformation vector thus allowing the transformed plant cell to grow in the presence of the selective pressure.

In some cases, adjustment of the growth regulating substances is required in order for the plant cell to differentiate into a mature plant. This may involve a number of steps in which the transformed plant cell is allowed to grow into an undifferentiated mass commonly referred to as a callus. This callus is then transferred to a medium which allows for the differentiation of said callus into organized plant structures and eventually mature plants. Alternatively, some procedures may involve the differentiation of the transformed plant cell directly into a structure such as a shoot which is then removed to media that allows for rooting and subsequent growth and flowering. For each individual plant species the choice of steps is determined experimentally.

E. Testing for the Presence and Expression of Antisense and Marker Genes

Plants which are regenerated from transformed plant cells are tested for the expression of the marker gene which is usually the gene that confers resistance to the selective agent. In the case of the commonly used gene neomycin phosphotransferase (NPT II) which confers resistance to kanamycin and the antibiotic G-418, gene expression is tested for by in vitro phosphorylation of kanamycin using techniques described in the available literature or by testing for the presence of the mRNA coding for the NPT II gene by northern blot analysis of RNA from the tissue of the transformed plant.

Expression of the antisense gene is monitored using the same northern blot techniques. Single stranded RNA probes which are either homologous to sense or antisense RNA transcripts are used to detect said transcripts in developing microspores such that the expression of the sense and antisense gene may be ascertained. It is preferable to use agarose gel electrophoresis to separate transcripts from the sense and antisense genes according to size and to do so under denaturating conditions. In the case where microspore specific gene expression of antisense genes is sought to be accomplished it is advisable to test for the expression of antisense genes in microspores and tissues other than microspores such as leaves, roots, etc. so that tissue specific gene expression of antisense genes in microspores can be verified.

The presence of a stably integrated sense or antisense gene in the genetic component of the plant cell may also be ascertained by using the so-called southern blot techniques. In this procedure, total cellular or nuclear DNA is isolated from the transformed plant or plant cell and preferably restricted with a restriction enzyme that usually cuts the vector used for transformation at discrete sites, thereby giving rise to discreet fragments. These discrete vector fragments can be detected in the nuclear or total DNA of the transformed plant or plant cells by employing standard gel electrophoresis and hybridization techniques.

Formation of microspores in plants which contain the antisense genes is monitored first by visual and microscopic examination of the anther structures. As maturation of the flower structure occurs, anther formation is expected to be delayed or completely inhibited such that no mature pollen grains are formed or released.

As the activity and hence effectiveness of any introduced recombinant DNA molecule is influenced by chance by the position of insertion of said molecule into the plant DNA the degree to which the inserted recombinant DNA may cause or render the plant sensitive to agents that cause reduced male fertility may vary from plant to plant. Accordingly, it will be necessary to select a plant which produces no functional pollen grains.

F. Hybrid Seed Production

Production of hybrid seed is accomplished by pollination of transformed male sterile plants with pollen derived from selected male fertile plants. Pollination can be by any means, including but not limited to hand, wind or insect pollination, or mechanical contact between the male fertile and male sterile plant. For production of hybrid seeds on a commercial scale in most plant species pollination by wind and by insect are preferred methods of pollination. Selection of plants for pollen donation is determined by standard crossing of different plants with subsequent analysis of the progeny and selection of the lines with the best combining ability. Restoration of fertility in the hybrid seed is, where warranted, accomplished by using the methodology detailed in the specific examples.

The invention is illustrated but not limited by the following examples:

EXAMPLE 1

This example relates to the isolation of a pollen specific promoter and a coding sequence (clone L 4) which is critical to pollen formation and expressed only in developing microspores. The promoter and coding sequence are isolated from, Brassica napus cv. Westar. The antisense DNA is placed under the control of the same polen specific promoter and used to transform plant cells derived from a plant of the species Brassica napus.

Two microspore specific genomic clones, L 4 and L 19, were isolated from a genomic library constructed from a plant of the species Brassica napus cv. westar by screening said library with probes constructed from RNA isolated from microspores, leaves, seeds and stems according to the methods specified above. The microspores were isolated from flower buds that were 3 to 5 mm in length.

Restriction maps of these two clones are shown in FIG. 1a and 1b. The 5' and 3' regions as well as the coding regions of these clones are shown and were determined by hybridization analysis according to the methods described above. The clone L 4 consists of two contiguous Eco RI restriction fragments of 2.5 and 5.7 Kb. Clone L 19 consists of a single 10.5 Kb Eco RI fragment. Not all restriction sites are shown in FIGS. 1a and 1b, only those relevant to the individual constructs detailed below.

The regions of the clones for which the nucleotide sequence has been determined are also indicated in FIGS. 1a and 1b. These nucleotide sequences are shown in FIGS. 2a–2c and 2d–2e, respectively. A DNA fragment that functions as a microspore specific promoter in transgenic plants was isolated from L 4 and consists of nucleotides 1–595 of the DNA sequence shown for L 4, in FIGS. 2a–2c. The ability of this DNA fragment to function as a microspore specific promoter in transgenic plants was determined by insertion of the entire 5.7 Kb Eco RI DNA segment of clone L 4 into tobacco plants and analyzing different tissue for the expression of the coding region of clone L 4 under high stringency conditions that allow for the specific detection of expressed coding sequence of clone L 4. Under these conditions, mRNA transcribed from the L 4 inserted DNA was only detectable in early uninucleate microspores isolated from the transgenic tobacco, and not in any other tissue examined which included stems, leaves, flower petals, filaments, stigma and stamen, large mature anthers. This particular inserted DNA segment contains the entire coding region of clone L 4 and 230 bases of 5' promoter sequence. This length of DNA represents the minimal amount of promoter DNA sequence needed to retain microspore specific promoter activity in transgenic tobacco. Provision of additional 5' promoter sequence does not alter the specificity of this DNA in terms of its functioning as a pollen specific promoter, it only increases the levels of pollen specific expression. Therefore, in order to maximize the levels of tissue specific gene expression from this specific DNA sequence, additional upstream region of the 5' region of clone L 4 was included in the DNA constructions listed below. A DNA fragment containing additional 5' sequences of the promoter region contained in clone L 4 was isolated as a Dde I fragment. This 1.9 Kb fragment was isolated in the following fashion: The Eco RI- Sst I fragment that encompasses the 5' region of the coding sequence and 235 nucleotides of the promoter were subcloned into the commercially available vector pGEM-4Z (sold by Promega Biotech Madison, Wis., U.S.A.) using the Eco RI and Sst I sites in the polylinker region. The resultant plasmid was named pPAL 0402. pPAL 0402 was digested with Eco RI and the 2.5 Kb Eco RI fragment of clone L 4 was ligated into this site, creating a plasmid that reconstructed the 5' region of the genomic clone L 4. This plasmid was named pPAL 0403. pPAL 0403 was digested with Dde I and the 1.9 Kb Dde I fragment that encompasses the promoter region of clone L 4 was isolated by gel elution, made blunt ended with Klenow fragment and subcloned into the Xba 1 site of pGEM-4Z previously made flush with Klenow treatment. Two orientations were obtained, the one shown in FIG. 3 was chosen for further constructions and was named pPAL 0408. This promoter fragment in pPAL 0408 contains the DNA sequences required for limiting the expression of any gene adjacent to the 3' end of this fragment solely to developing microspores. At the extreme 3' end of this fragment is the start of transcription site so that any DNA sequence placed at this end of the fragment will be transcribed and will contain a 69 (+or −2 bp) untranslated leader sequence without any ATG initiation codon. A cassette transformation vector using this promoter fragment was constructed using the binary transformation vector BIN 19 (obtained from the Plant Breeding Institute and described in Beyan, M., 1984, Nucl. Acids Res. 12:8711–8721) and adding to BIN 19 the hopaline synthase polyadenylation signal (nos ter) isolated as a Sst I - Eco RI 260 bp restriction fragment from the plasmid pRAJ 221 (available from Clonetech Laboratories, Palo Alto, Calif., USA) and inserting this nos ter fragment into the Sst I - Eco RI restriction sites of BIN 19. The resultant plasmid vector was called PAL 1001. The promoter from pPAL 0408 was added to PAL 1001 by cutting pPAL 0408 with Sal I and Sst I and cloning this promoter-polylinker containing fragment in the vector PAL 1001 using the Sal 1 and Sst I sites of PAL 1001. A binary transformation vector PAL 1107 was constructed.

The details of the construction of PAL 1107 are shown in FIG. 3. This vector has (in a 5' to 3' order) the promoter from clone L 4, followed by a portion of the polylinker from PGEM-4Z containing the following restriction sites: Barn HI, Stoa I, Kpn I and Sst I followed then by the nos ter. This vector allows for the convenient insertion of DNA fragments for transcription under the control of the pollen specific promoter isolated from clone L 4.

To this PAL 1107 vector was added a coding region fragment of clone L 4 in the antisense orientation by digesting pPAL 0402 with Bam HI and Hinc II and ligating this 1.68 KG coding region restriction fragment to Bam HI - Sma 1 cut PAL 1107. This construction was mobilized into Agrobacterium tumefaciens. The Agrobacterium strain GV 3101 carrying the Ti plasmid pMP 90 (Koncz, C. and Schell, J. 1986, Mol. Gen. Genet. 204: 383–396 ) to provide the Vir functions in trans was used as a recipient this binary vector (PAL 1107 containing the antisense restriction fragment) by delivery of the binary vector through tripartite mating and kanamycin selection minimal media. Binary vectors allowed for the selection of transformed plants by the virtue of carrying the NPT II (neomycin phosphotransferase) gene under the control of the nos promoter providing for resistance to kanamycin and G418 in transformed plant cells.

Transformation of *Brassica napus* plants with this antisense gene was accomplished by cocultivation of thin epidermal layers from stems of *Brassica napus*, cv. Westar. The cocultivation was performed using surface sterilized stem epidermal layer peels as follows. The upper three internodes of the stem of plants that had fully developed bud clusters but whose buds had not yet opened (but were within 1-3 days of doing so) were surface sterilized by rinsing in 70% ethanol for 5 to 6 seconds followed by 2% sodium hypochlorate for 10 minutes and then three times in sterile distilled water.

Segments were cultured for 1 day on modified MS media in which $NH_4NO_3$ was replaced with 60 mM $KNO_3$ and having in addition B5 vitamins with 40 mg per 1. of FeEDTA as a source of iron, 0.5 mg per 1 - naphthalene acetic acid and 10 mg per 1 benzyl adenine with 3% sucrose and 0.8% agar, pH 5.8. This modified medium is hereinafter referred to as EPL. All cultures were maintained under continuous light (approximately 70 uE per sq.m per sec). After this period of time, the explants were removed from the surface of the culture media and exposed to the Agrobacterium strain carrying PAL 1107 into which the 1.68 Kb Bam HIII - Hinc III fragment of L 4 was inserted. This was done by using sterile forceps to place the explant in contact for a few moments with a confluent layer of bacteria that was growing on the surface of a petri plate. The bacteria were grown in minimal media containing kanamycin at 100 ugs. per ml. It is also possible to expose for a few seconds the epidermal layers to the bacteria in liquid culture [liquid media such as LB-MG (Beringer, J. E., 1974, Jour, Gen. Microbiol. 84: 188–198) containing 100 ugs. per ml. kanamycin and 20 uM acetosyringone], with similar results. The epidermal layers were blotted on sterile filter paper and placed on plates that contained EPL. These plates were covered with a layer of tobacco cells (the feeder layer) from a cell suspension of *Nicotiana debneyi* and overlayed with sterile filter paper upon which the epidermal layers were placed. After a maximum of three days of cocultivation with the Agrobacterium, the segments were transferred to EPL media without a feeder layer or filter paper. This media contained in addition to the normal components, 100 ug per ml of kanamycin sulfate for selection of transformed plant cells and 500 ug per ml of cefotaxamine to kill the Agrobacterium bacteria.

Shoots which were regenerated from the epidermal layers were subsequently tested for the activity of the NPT II enzyme. The shoots that tested positive for the NPT II enzyme were rooted on B5 media containing 2% sucrose, 0.8% agar and 0.5 mg per 1. of both indole-3-acetic acid and - naphthalene acetic acid. After rooting, the plants were transferred to soil and placed in a misting chamber for 7 days. The plants were then transferred to a growth chamber where they were allowed to develop and flower.

Southern blot analysis of DNA taken from these plants confirmed the presence of the antisense gene.

EXAMPLE 2

In this example we use the same promoter as in example 1 and a different pollen specific sense coding sequence (clone L 19) to construct the antisense gene and transform plant cells derived from a plant of the species *Brassica napus*.

To the vector PAL 1107 wa added a 1.3 Kb Hind I II restriction fragment containing coding sequence from clone L 19. This fragment was first made blunt by Klenow treatment and this blunt ended fragment was cloned into the unique Sma 1 site of PAL 1107. Clones containing this 1.3 Kb Hind III fragment in the antisense orientation were chosen and used for the transformation of *Brassica napus* stem epidermal layer peels as described above.

EXAMPLE 3

In this example, we transform tobacco which was previously transformed to hygromycin resistance with and antisense that blocks the hygromycin resistance gene under the control of a pollen specific promoter derived from *Brassica napus* (clone L 4).

The 0.8 Kb Barn HI restriction endonuclease fragment encoding the hygromycin phosphotransferase gene (Gritz and Davies, 1983 Gene 25:179–185) was isolated from the plasmid pVU1011 supplied by S. Scofield of the Plant Breeding Institute, Cambridge, U.K.. pVU 1011 is BIN 19 into which has been added a CaMV 35S promoter controlling the expression of the hygromycin phosphotransferase gene followed by the nos terminator. The 0.8 Kb Bam HI restriction endonuclease fragment was ligated into the single Bam HI restriction endonuclease site in PAL 1107 previously described in example 1. Clones containing the 0.8 kb hygromycin phosphotransferase gene fragment in PAL 1107 were restriction mapped and one which contained said fragment in the antisense orientation was isolated and named PAL 1107HYGAS.

This vector was used for the production of male sterile plants by transformation of a plant that had been previously transformed to hygromycin resistance with a vector called pGUS-HYG. We now turn to the construction of pGUS-HYG. pGUS-HYG is pVU10 11 in which the NPT II gene (neomycin phosphotransferase gene) is inactivated by insertion of a DNA fragment from pRAJ 221 into this NPT II gene. Since the intact pVU1011 vector confers hygromycin resistance in addition to kanamycin resistance we inactivated the NPT II gene in order to produce a vector which confers only hygromycin resistance. To insert a DNA fragment into the NPT II gene the pVU1011 plasmid was partially digested with Sph I restriction endonuclease. The cut pVU1011 was made blunt ended by the use of Klenow fragment. The DNA fragment from pRAJ 221, which contains the CaMV 35S promoter controlling the expression of the GUS (beta-glucuronidase) gene followed by the nos terminator, was isolated by restricting pRAJ 221 with Hind III and Eco RI restriction endonucleases and making this fragment blunt ended with Klenow fragment. Said fragment was then ligated to the partially digested blunt ended pvU1011. Clones containing the GUS gene in the middle of the NPT II gene in pVU1011 were identified by restriction endonuclease analysis. Such a clone confers resistance in the plant only to hygromycin and not to kanamycin or G418 by virtue of the fact that the NPT II gene is interrupted by the presence of the GUS gene. The inserted GUS gene provides a convenient expression marker for plant transformation. This clone was named pGUS-HYG.

We now turn to the transformation of tobacco leaf discs with the vectors pGUS-HYG and PAL 1107HYGAS. Both pGUS-HYG and PAL 1107HYGAS were mobilized into *Agrobacterium tumifaciens* GV 3101 containing pMP-90 to provide vir functions in trans by tripartite mating and selection on minimal media. Leaf discs were excised from leaves which were medium green and less than 8 inches long and were surface sterilized by exposure to ethanol for 5 to 6 seconds and subsequent exposure to a 1% solution of sodium hypochlorite for a few minutes or until the cut edge of the petiole turned white. Leaves were rinsed with sterile distilled water. Discs approximately 0.5 to 0.7 cm large were excised from the leaves with a sterile cork borer. The leaf discs were placed on media consisting of 0.8% agar, MS salts, B5 vitamins, 3% sucrose, 1 mg per 1. of benzyl adenine and 0.1 mg per 1. of - naphthalene acetic acid. Discs were placed upper epidermis side down on this media. Cultures were maintained on a 16 hour photoperiod at 25° C. After one day of culture, discs were removed and placed in a 10 ml overnight culture of Agrobacterium containing pGUS-HYG. The discs and bacteria were gently shaken for a few moments to insure bacterial contact with the leaf discs. The leaf discs were removed and blotted dry on sterile filter paper and placed on new media. This media contained cefotaxamine at 500 ugs. per ml., in addition to the ingredients of the first culture media, in order to kill the bacteria and also hygromycin at 50 ugs. per ml. for selection of transformed plant cells that carried the hygromycin phosphotransferase gene. Shoots were allowed to regenerate on this selective media from these explants. After 3 to 8 weeks coculture on selective media, shoots were large enough to be transferred to rooting media. Plants were rooted on B5 media that contained: 0.8% agar, 2% sucrose and 0.5 mg per ml. of both naphthalene acetic acid and indole acetic acid. After rooting, plants were transferred to soil and kept in a misting chamber for 7 days and subsequently transferred to greenhouse growth facilities. Plants were fertilized weekly and watered daily until maturity.

Transformed tobacco containing the sense hygromycin gene from pGUS-HYG was re-transformed with PAL 1107HYGAS using the leaf disc procedure described above. Retransformed plant cells were exposed to hygromycin at 50 ugs. per ml. and kanamycin at 300 ugs. per ml. to select for the presence of both the hygromycin phosphotransferase gene from pGUS-HYG and the NPT II gene contained in PAL 1107HYGAS. Regenerated plants were obtained from said cells that were resistant to both antibiotics and were grown in the presence of 50 ugs. per ml. of hygromycin by rooting in one-tenth strength MS salts in 0.8% agar containing hygromycin. Optionally it is possible to do a double transformation using both PAL 1107HYGAS and pGUS-HYG, by coculturing the plant explants with both bacteria containing each vector and selecting for doubly transformed cells using both kanamycin and hygromycin in the media.

EXAMPLE 4

In this example we repeat the procedure used in example 3 with *Brassica napus*.

The vectors described in example 3 were also used for the production of male sterile plants in *Brassica napus*. The vectors PAL 1107 HYGAS and pGUS-HYG were used for transformation of thin stem epidermal layers of *Brassica napus*, cv. Westar stems. The cocultivation was performed using surface sterilized stem epidermal layer peels as described in example 1. The vector pGUS-HYG was used for an initial transformation, then plants resistant to hygromycin were recovered.

For the production of male sterile plants in the plasmid PAL 1107 HYGAS was used to retransform *Brassica napus* stem epidermal peels from plants that had been previously transformed to hygromycin resistance using the hygromycin phosphotransferase gene in pGUS-HYG.

Retransformed *Brassica napus* plant cells containing the sense hygromycin gene from pGUS-HYG and the antisense hygromyc in gene in PAL 1107 HYGAS were exposed to hygromycin at 10 ugs. per ml. and kanamycin at 100 ugs. per ml. to select for the presence of both the hygromycin phosphotransferase gene from pGUS-HYG and the NPT II gene contained in PAL 1107HYGAS. Regenerated plants were obtained from said cells that were resistant to both antibiotics.

EXAMPLE 5

In this example, we repeat the procedure used in example 3 with tomato.

The vectors described in example 3 were used for the production of male sterile plants in tomato, *Lycopersicon esculentum*. The vectors PAL 1107HYGAS and pGUS-HYG were used. Each vector was used individually for transformation by first mobilizing the vector into *Agrobacterium tumefaciens* LBA 4404 via triparental mating (Beyan, M., 1984, Nucl. Acids Res. 12:8711–8721). Tomato plants resistant to hygromycin were first obtained by using pGUS-HYG to transform tomato leaf discs according to published procedures (Horsch et al, 1985 Science 227:1229-1231). According to this method, leaves are surface sterilized by rinsing with 70% ethanol for a few moments followed by soaking in a solution of 1% sodium hypochlorite for approximately 10 minutes or until the edge of the leaf bleaches and finally rinsing in sterile water. Discs are excised from the leaf with a sterile cork borer and incubated for one minute with gentle shaking in a solution of Agrobacterium containing the transformation vector grown overnight in standard bacterial media (LB) at pH 5.6. The discs were blotted dry and placed on a feeder layer as described in example 1 that were present on a media containing MS based salts, 0.8% agar, 3 mg per ml. benzyladenine and 0.3 rag. per ml. indole-3-acetic acid for a period of three days. After this time, discs were transferred to the same media without a feeder layer and containing in addition to the normal components, 500 ugs.. per ml. cefotaxamine and 100 ugs. per ml. kanamycin for vectors containing kanamycin resistance as a selectable marker. For vectors which confer hygromycin resistance, kanamycin was omitted and 10 ugs. per ml. of hygromycin was used. Shoots which regenerated were transferred to rooting media (B5 based salts, 0.5 mg./per 1 indole-3-acetic acid, and - napthalene acetic acid with 0.8% agar) and allowed to develop into mature plants.

For the production of male sterile plants, PAL 1107HYGAS was used to re-transform leaf tissue taken from tomato plants that were previously transformed to hygromycin resistance using the hygromycin phosphotransferase gene in pGUS-HYG. Retransformed tomato plant cells containing the sense hygromycin gene from pGUS-HYG and the antisense hygromycin gene from PAL 1107HYGAS were selected for with hygromycin at 10 ugs. per ml. and kanamycin at 100 ugs. per ml. to select for the presence of both the hygromycin phosphotransferase gene from pGUS-HYG and NPT II gene contained in PAL 1107HYGAS. Plants were regenerated from said cells.

EXAMPLE 6

In this example, we transform a plant of the species *Brassica napus* with a recombinant DNA molecule comprising a sequence coding for the Ricin A chain toxin and a pollen specific promoter derived from *Brassica napus* (clone L 4).

A published sequence of a *Ricinus communis* agglutinin gene (Roberts et al., JBC, 260:15682–15686) was used to construct a ricin specific probe and isolate the ricin gene from a genomic library of *Ricinus zanzibarensis* DNA. A DNA fragment coding for the mature A chain sequence (amino acid 2 through 262) was generated by exonuclease digestion of a 2.3 kb Eco RI restriction endonuclease fragment that contained the entire A chain coding sequence and a portion of the B chain of ricin subcloned as an Eco RI restriction endonuclease fragment in pGEM 4Z. The construction of the clone containing the A chain coding region is shown in FIG. 4. Deletion of the coding sequences of the B-chain ricin was done as follows. The subclone was cut with Kpn I restriction endonuclease and Sac I restriction endonuclease and unidirectionally digested with Exonuclease III. The digested plasmid was treated with S1 nuclease and Klenow fragment, religated in the presence of a universal translation terminator (purchased from Pharmacia P-L Biochemicals, Dorval, Quebec, Canada) which has translation stop codons in all three reading frames. Deleted subclones were recovered and individual subclones were sequenced. One such subclone was found to contain a deletion that encompassed the internal portion of the B chain upstream to the codon coding for amino acid 262 (proline) of the A chain in the published sequence. The sequence of the deletion end point, reading 5' to 3', is as follows:

```
      end          universal
     codon        terminator           polylinker
5'-CCG—GCTTAATTAATTAAGC—CGGGGATCCTTAG-3'
                                       Bam HI site
```

As shown above, the polylinker contains a Bam HI restriction endonuclease site. We also determined that there was a Bam HI restriction site upstream from the mature A chain in this clone. This deletion subclone was digested with Bam HI restriction endonuclease. This Bam HI restriction endonuclease fragment which codes for the A chain of Ricin was subcloned into Barn HI restriction endonuclease cut pGEM-3. The inserted fragment was positioned so that the 5' end of the ricin A chain gene was next to the Xba I restriction endonuclease site in pGEM 3. This subclone was unidirectionally deleted with Exonuclease III following digestion of the clone with Pst I and Sal I restriction endonucleases. Following digestion, the digested DNA was treated with S1 nuclease and Klenow fragment, and was religated in the presence of a palindromic oligonucleotide linker (sequence being: 5' - CATCGGATCCGATG - 3') such that the entire deletion could be excised from the plasmid with Bam HI restriction endonuclease and contains an ATG initiation codon. Deletion subclones were picked and sequenced and one was chosen that was deleted to amino acid residue 2 and had the sequence (reading from polylinker into the 5' end of the gene) 5-CCC GGG GAT CCG ATG TTC-3' whereas the ATG codon specifies an initiation codon in frame to the mature A chain sequence and was introduced by the insertion of the palindromic oligonucleotide linker and the last three nucleotides of that sequence code for a phenylalanine amino acid residue that is the second residue in the mature A chain of ricin. This was deduced by comparison of the sequence with previously published reports of the sequence of ricin. This clone was named pPAL AC and contained the ricin A chain gene excisable as a Bam HI fragment. This Bam HI restriction endonuclease fragment was subsequently cloned into PAL 1107 by the use of the single Barn HI restriction endonuclease site of the polylinker of PAL 1107. The 3' end of this A chain gene contained at its 3' end the three frame translation terminator such that only the A chain protein would be produced by this construct wherein the C terminal amino acids are: pro-ala-(stop). In between these newly created N-terminal and C-terminal amino acid residues was the mature ricin A chain amino acid sequence as coded for by the deleted ricin gene. Vectors with this recombinant ricin gene in the opposite (antisense) orientation were also recovered (such vectors containing the antisense recombinant ricin gene are referred to as PAL 1107RICAS). Clones containing the recombinant ricin gene under control of the microspore specific promoter in PAL 1107 and in the sense orientation were named PAL 1107RIC.

The PAL 1107RICAS and PAL 1107RIC were used to transform plants of the species *Brassica napus* according to the method described in example 1.

EXAMPLE 7

In this example, we use the same procedure used in example 6, however, we use a truncated version of Ricin A chain gene.

A truncated version of the ricin A chain gene of pPAL-AC was isolated by digesting pPAL-AC with Barn HI and Bgl II. This releases an A chain fragment containing a Bam HII site preceeding the ATG start, and the first 196 amino acid codons of the mature A chain sequence. This fragment was cloned into the Bam HI site of PAL 1107 and a clone containing the gene in the sense orientation was recovered. This clone (PAL 1107 containing the truncated A chain gene) was digested with Sma I, phosphorylated with alkaline phosphatase and religated in the presence of the universal translation terminator described in example 6. Clones containing this terminator inserted into the Sma I site were recovered and were named PAL 1107 AC. PAL 1107AC was used to transform *Brassica napus* stem epidermal layer peels as described in example 1.

EXAMPLE 8

In this example, we use the same procedure used in example 7 to transform tobacco.

The vector PAL 1107AC was used to transform tobacco leaf discs as described in example 3. Transformed plants containing the truncated ricin A chain gene were recovered.

EXAMPLE 9

In this example, we use the same procedure used in example 7, to transform tomato.

The vector PAL 1107AC was used to transform tomato leaf discs as described in example 5.

EXAMPLE 10

In addition to the procedure used in tobacco in example 8, in this example, we construct an antisense coding sequence of the Ricin A chain gene and regulate its expression using the same pollen specific promoter.

The vectors PAL 1107RIC and PAL 1107RICAS were used to produce male sterile and restoration lines in tobacco.

Tobacco leaf discs were transformed with these two vectors using procedures outlined in example 3. Transformed regenerated plants containing the antisense and sense ricin A chain genes were recovered.

EXAMPLE 11

In this example, we repeat the procedure used in example 10 with tomato.

The vectors PAL 1107RIC and PAL 1107RICAS were used to produce male sterile and restorer lines in tomato. Tomato leaf discs were transformed with these two vectors using procedures outlined in example 5.

EXAMPLE 12

In this example, we inactivate a pollen specific gene derived from *Bassica napus* (clone L 19) using antisense DNA under the control of the CaMV 35S constitutive promoter.

The use of antisense RNA to control fertility can also be accomplished by the use of a promoter that is functional in all tissues such that any gene placed under control of this promoter will be transcribed in all cells of the plant. In this example, the Cauliflower Mosaic Virus 35S promoter in the plasmid pRAJ 221 was used to produce antisense RNA by directing the transcription of the 1.3 Kb Hind III restriction endonuclease fragment containing coding sequence from L 19 cloned in the antisense orientation to this promoter. This was accomplished by digesting pRAJ-221 with Hind III and Xba I and inserting this Callflower Mosaic Virus 355 promoter fragment into Hind III- Xba I cut PAL 1001 described above. This produced a vector (PAL 1007) into which fragments can be conveniently cloned in the portion of the polylinker from BIN 19 located between the Cauliflower Mosaic Virus 35S promoter and the nos ter. Sma 1 was used to cut PAL 1007 and the 1.3 Kb Hind III fragment from clone L 19 was isolated, made blunt end by Klenow treatment and inserted into this Sma I site of PAL 1007. Clones containing the fragment in the antisense orientation were chosen and used to transform *Brassica napus* thin stem epidermal layers of cv. Westar as outlined in example 1.

EXAMPLE 13

In this example, we inactivate a different pollen specific gene derived from *Brassica napus* (clone L 4) using antisense DNA under the control of CaMV 35S constitutive promoter.

The use of antisense RNA to control fertility can be accomplished using a promoter functional in all tissues such as that described in example 12. The vector PAL 1107 was cut with Bam HI and Sma 1. To this vector was added the 1.68 Kb Bam HI - Hinc II fragment of clone L 4. This vector (PAL 1311) carries the coding region of L 4 in the antisense orientation. PAL 1131 wa used to transform *Brassica napus* stem epidermal layer peels as described in example 1.

EXAMPLE 14

In this example, we inactivate a pollen specific gene derived from *Brassica napus* (clone L 19) using antisense DNA under the control of the inducible heat shock promoter fragment of the Drosophila HSP 70 gene.

The inducible heat shock promoter fragment of the Drosophila HSP 70 gene in pPW 229 ( obtained from Meselson, M., Harvard University and described in Livak et al., 1978 Proc. Natl. Acad. Sci. USA 75: 5613–5617) was isolated as a Hind III - Pst I restriction endonuclease fragment and cloned into Hind III - pst I restriction endonuclease cut pGEM 4Z. The heat shock promoter fragment was excised as a Hind III - Sma I fragment and cloned into Hind III -Sma I cut PAL 1001. This produced a vector (PAL 1009) that contains a heat shock promoter followed by a portion of the polylinker and the nos ter. The Sma I restriction endonuclease site in PAL 1009 was used for the cloning of a 1.3 Kb Hind III restriction endonuclease fragment containing coding sequence from L 19 following the making of this 1.3 Kb fragment blunt end with Klenow fragment. The clone containing sequence in the antisense orientation was determined by restriction mapping. This vector was named PAL 1403. This vector was used for transformation of *Brassica napus,* following procedures detailed in example 1.

EXAMPLE 15

In this example, we inactivate the actin gene, a gene that is critical to cellular function and development in all metabolically competent cells. We use an antisense version of said actin gene under the control of a pollen specific promoter derived from *Brassica napus* (clone L 4).

The use of a pollen specific promoter to direct the synthesis of antisense RNA causing male sterility was accomplished by inserting an actin gene in the antisense orientation under the control of the pollen specific promoter in PAL 1107 by using pSAc3, a soybean actin clone to provide an actin coding region. (pSAc3 was provided by R. Meagher) The coding region of actin was isolated as a Eco RI-Taq I fragment made blunt ended and inserted into Sma I cut PAL 1107. Clones containing the gene in the antisense orientation were chosen and named PAL 1107ASac. This vector was used to transform *Brassica napus* stem epidermal layer peels using the method outlined in example 1.

EXAMPLE 16 In this example we use the same procedure used in example 15 with tomato.

PAL 1107ASac was used to transform tomato leaf discs using the method of example 5.

EXAMPLE 17

In this example, we use the same procedure used in example 15 with tobacco.

PAL 1107Sac was used to transform tobacco leaf discs using the method described in example 3.

We claim:

1. A method of producing hybrid seed from plants from a species of pollen-producing plants that is capable of being genetically transformed, comprising the steps of:

(a) producing a genetically transformed plant by:

(i) inserting into the genome of a plant cell of said species that can be regenerated into a differentiated, whole plant;

I. a sense gene that confers on said plant resistance to a herbicide or an antibiotic
and
II. a recombinant DNA molecule comprising:
  (A) a DNA sequence that codes for RNA that is complementary to the RNA sequence encoded by said sense gene
  and
  (B) a pollen-specific Brassica promoter which functions in said plant cell to cause transcription of said DNA sequence into RNA,
(ii) obtaining a transformed plant cell which has been transformed with said sense gene and said recombinant DNA and
(iii) regenerating from said transformed plant cell a plant that is genetically transformed with said sense gene and said recombinant DNA molecule such that (A) said recombinant DNA molecule interferes with the expression of said sense gene and (B) said genetically transformed plant can be rendered male sterile by said herbicide or antibiotic;
(b) increasing the number of genetically transformed plants by:
  (i) fertilizing said genetically transformed plant with pollen produced by a suitable male fertile plant and obtaining seed which, when germinated, yields a plurality of genetically transformed plants; or
  (ii) clonally propagating said genetically transformed plant to obtain a plurality of genetically transformed plants; and
(c) effecting a hybrid cross by pollinating said genetically transformed plants with pollen from suitable male fertile plant donors.

2. The method of claim 1, wherein growing said genetically transformed plant in isolation from the same herbicide or antibiotic to produce a self-fertile plant,
(ii) permitting self-fertilization and
(iii) growing seed of such self-fertile plant over a number of generations in isolation from the same herbicide or antibiotic to increase the number of genetically transformed plants;
and wherein step (c) is accomplished by: effecting a hybrid cross by growing said genetically transformed plants alongside plants of a suitable line of male fertile donors in the presence of the same herbicide or antibiotic during pollen formation to produce male sterile plants and to permit pollination of said male sterile plants.

3. A method of producing a plant which carries the male sterile trait, which method comprises the steps of:
(a) transforming a cell of a pollen-producing plant which is from a species of pollen-producing plants that is capable of being regenerated into a differentiated whole plant, with a sense gene that confers on said plant resistance to a herbicide or an antibiotic;
(b) regenerating from said transformed plant cell a genetically transformed plant which is resistant to the same herbicide or antibiotic;
(c) inserting a recombinant DNA molecule into the genome of a plant cell of said herbicide- or antibiotic-resistant plant which is capable of being regenerated into a differentiated whole plant, wherein said recombinant DNA molecule comprises:
  (i) a DNA sequence that codes for RNA that is antisense relative to the RNA sequence encoded by said sense gene; and
  (ii) a pollen-specific Brassica promotor which functions in said plant cell to cause transcription of said DNA sequence into RNA;
(d) obtaining a transformed plant cell; and
(e) regenerating from said transformed plant cell a genetically transformed plant which has been transformed with the sense gene described in step (a) and the recombinant DNA molecule described in step (c) above such that said recombinant DNA interferes with the expression of said sense gene and said genetically transformed plant can be rendered male sterile by said herbicide or antibiotic.

4. A method of producing a hybrid seed with restored male fertility from plants of a species of pollen-producing plants that is capable of being genetically transformed, comprising the steps of:
(a) producing a plant which carries a male sterile trait by:
  (i) inserting into the genome of a plant cell of said species that can be regenerated into a differentiated, whole plant:
    I. a sense gene which confers on said plant resistance to a herbicide or an antibiotic and
    II. a recombinant DNA molecule comprising
      (A) a DNA sequence that codes for RNA that is antisense relative to the RNA sequence encoded by said sense gene; and
      (B) a pollen-specific Brassica promoter which functions in said plant cell to cause transcription of said DNA sequence into RNA,
  (ii) obtaining a plant cell of a plant which has been transformed with the sense gene and recombinant DNA molecule described in step (i) above and
  (iii) regenerating from said transformed plant cell a genetically transformed plant which is transformed with the sense gene and recombinant DNA molecule described in step (i) above such that said recombinant DNA molecule interferes with the expression of said sense gene and said genetically transformed plant can be rendered male sterile by said herbicide or antibiotic;
(b) increasing the number of genetically transformed plants by:
  (i) growing the genetically transformed plant described in step (a)(iii) above in isolation from the same herbicide or antibiotic to produce a self-fertile plant,
  (ii) permitting self-fertilization and
  (iii) growing seed of such self-fertile plant over a number of generations in isolation from the same herbicide or antibiotic to increase the number of genetically transformed plants;
(c) exposing said genetically transformed plants to said herbicide or antibiotic to produce male sterile plants; and
(d) effecting a hybrid cross by pollinating said male sterile plants with pollen derived from suitable male fertile donors.

5. The method of claim 2, wherein said pollen-specific Brassica promotor consists of a DNA sequence which comprises the sequence of nucleotides 1–595 in FIG. 2a.

6. The method of claim 2, wherein said herbicide or antibiotic is hygromycin and wherein said sense gene comprises:
   (i) a pollen-specific Brassica promotor;
   (ii) a DNA sequence which codes for the production of hygromycin phophotransferase; and
   (iii) a termination sequence which defines a termination signal during transcription of said DNA sequence.

7. The method of claim 1, wherein said species is Brassica napus or Brassica campestris.

8. The method of claim 1, wherein said pollen-producing plant is of the genus Brassica.

9. The method of claim 1, wherein said pollen-producing plant is of the family Cruciferae.

10. The method of claim 1, wherein said pollen-producing plant is of the family Solanaceae.

11. A plant which has been transformed with:
   (a) a sense gene which confers on said plant resistance to a herbicide or an antibiotic; and
   (b) a recombinant, double-stranded DNA molecule comprising:
      (i) a DNA sequence that codes for RNA that is antisense relative to the RNA sequence encoded by said sense gene;
      (ii) a pollen-specific Brassica promotor which functions in said plant cell to cause transcription of said DNA sequence into RNA; and
      (iii) a terminator sequence which defines a termination signal during transcription of said DNA sequence.

12. Hybrid seed containing DNA comprising:
   (a) a sense gene which confers on a plant grown from said seed resistance to a herbicide or an antibiotic; and
   (b) a recombinant double stranded DNA molecule comprising:
      (i) a DNA sequence that codes for RNA that is antisense relative to the RNA sequence encoded by said sense gene;
      (ii) a pollen-specific Brassica promotor which functions in said plant cell to cause transcription of said DNA sequence into RNA; and
      (iii) a terminator sequence which defines a termination signal during transcription of said DNA sequence.

13. A cell line produced from genetically transformed cells that are the product of a process comprising the steps of (i) inserting into the genome of a plant cell of a pollen-producing plant a recombinant DNA sequence comprised of antisense DNA that renders developing pollen grains susceptible to a herbicide or to an antibiotic, wherein said plant is capable of regeneration into a differentiated, whole plant and wherein said antisense DNA is under the control of a pollen-specific Brassica promoter; and then (ii) obtaining a transformed plant cell of said plant.

14. The method of claim 2, wherein said pollen-specific Brassica promotor is the promotor of the sense gene.

15. The method of claim 3, wherein said pollen-specific Brassica promotor consists of a DNA sequence which comprises the sequence of nucleotides 1–595 in FIG. 2a.

16. The method of claim 4, wherein said pollen-specific Brassica promotor consists of a DNA sequence which comprises the sequence of nucleotides 1–595 in FIG. 2a.

17. A method as claimed in claim 2, wherein said recombinant DNA molecule comprises a terminator sequence which defines a termination signal during transcription of said DNA sequence.

18. A method as claimed in claim 3, wherein said recombinant DNA molecule comprises a terminator sequence which defines a termination signal during transcription of said DNA sequence.

19. A method as claimed in claim 4, wherein said recombinant DNA molecule comprises a terminator sequence which defines a termination signal during transcription of said DNA sequence.

20. A method of producing a male sterile plant, or a plant carrying a male sterile trait, which method comprises the steps of:
   (i) introducing into the genome of one or more plant cells of a plant, wherein said plant is of a species of pollen-producing plants that is capable of being genetically transformed, one or more recombinant DNA molecules as claimed in claim 18;
   (ii) selecting a plant cell into which the recombinant DNA molecule is stably integrated; and
   (iii) regenerating a plant which is male sterile or carries the male sterile trait from the selected plant cell.

21. The method of claim 20, wherein said species is of the family Cruciferae.

22. The method of claim 21, wherein said species is Brassica napus or Brassica campestris.

23. A method of producing hybrid seed from a plant of a species of pollen-producing plants that is capable of being genetically transformed, which method comprises the steps of:
   (i) inserting into the genome of one or more plant cells of said plant one or more recombinant DNA molecules as claimed in claim 18;
   (ii) selecting a plant cell into which the recombinant DNA molecule is stably integrated;
   (iii) regenerating from the selected plant cell a plant which carries the male sterile trait;
   (iv) increasing the number of plants which carry the male sterile trait;
   (v) exposing said plants which carry the male sterile trait to a herbicide or an antibiotic which renders said plants male sterile; and
   (vi) crossing a male sterile plant so obtained with a male fertile plant and obtaining hybrid seed.

24. The method of claim 23, wherein said species is of the family Cruciferae.

25. The method of claim 23, wherein step iv) comprises producing progeny by selfing a plant which carries the male sterile trait; then selecting from among said progeny a plant which is homozygous for the male sterile trait; and increasing the homozygous plant by selfing in isolation.

26. The method of claim 23, wherein step iv) comprises providing progeny by culturing anther tissue or isolated microspores from a plant which carries the male sterile trait; selecting from among said progeny a plant which is homozygous for the trait; and increasing the homozygous plant by selfing in isolation.

27. The method of claim 20, wherein said species is of the family Solanacea.

28. The method of claim 20, wherein said species is of the genus Brassica.

29. The method of claim 23, wherein said species is of the family Solanacae.

30. The method of claim 23, wherein said species is of the genus Brassica.

31. A method according to claim 2, wherein said sense gene is expressed in developing microspores.

32. A method according to claim 31, wherein said sense gene is expressed in early uninucleate microspores.

* * * * *